United States Patent
Heilek et al.

(10) Patent No.: US 7,999,120 B2
(45) Date of Patent: Aug. 16, 2011

(54) PROCESS FOR CONTINUOUSLY REMOVING A TARGET PRODUCT X IN THE FORM OF FINE CRYSTALS

(75) Inventors: Jörg Heilek, Bammental (DE); Peter Schlemmer, Eisenberg (DE); Ulrich Hammon, Mannheim (DE); Klaus Joachim Müller-Engel, Stutensee (DE)

(73) Assignee: BASF SE, Ludwigshafen (DE)

( * ) Notice: Subject to any disclaimer, the term of this patent is extended or adjusted under 35 U.S.C. 154(b) by 249 days.

(21) Appl. No.: 12/209,594

(22) Filed: Sep. 12, 2008

(65) Prior Publication Data

US 2009/0076284 A1    Mar. 19, 2009

Related U.S. Application Data

(60) Provisional application No. 60/971,969, filed on Sep. 13, 2007, provisional application No. 60/972,023, filed on Sep. 13, 2007, provisional application No. 60/971,994, filed on Sep. 13, 2007.

(30) Foreign Application Priority Data

| Sep. 13, 2007 | (DE) | 10 2007 043 748 |
| Sep. 13, 2007 | (DE) | 10 2007 043 758 |
| Sep. 13, 2007 | (DE) | 10 2007 043 759 |

(51) Int. Cl.
*C07D 227/00* (2006.01)
*C07C 51/43* (2006.01)
*C07C 7/14* (2006.01)

(52) U.S. Cl. ............... 548/540; 562/600; 585/812

(58) Field of Classification Search ............... 548/540; 562/600; 585/812
See application file for complete search history.

(56) References Cited

U.S. PATENT DOCUMENTS

| 6,939,991 | B2 | 9/2005 | Thiel et al. |
| 7,112,695 | B2 | 9/2006 | Eck et al. |
| 7,279,075 | B2 | 10/2007 | Thiel et al. |
| 7,393,436 | B2 | 7/2008 | Eck et al. |
| 2006/0199976 | A1 | 9/2006 | Heilek et al. |
| 2008/0183014 | A1 | 7/2008 | Diefenbacher et al. |

FOREIGN PATENT DOCUMENTS

| DE | 103 32 758 A1 | 5/2004 |
| DE | 103 00 816 A1 | 7/2004 |
| DE | 10 2005 009 890 A1 | 9/2006 |
| DE | 10 2007 004 960 A1 | 7/2008 |
| WO | WO 01/77056 A1 | 10/2001 |
| WO | WO 2004/035514 A1 | 4/2004 |

OTHER PUBLICATIONS

"Kristallisator mit Wärmeübertragungselementen", Research Disclosure Database No. 496005, Aug. 2005, 6 pages.
"Kristallisator mit Wärmeübertragungselementen", Research Disclosure Database No. 479008, 7 pages.

*Primary Examiner* — Rebecca Anderson
*Assistant Examiner* — Samantha Shterengarts
(74) *Attorney, Agent, or Firm* — Oblon, Spivak, McClelland, Maier & Neustadt, L.L.P.

(57) ABSTRACT

A process for continuously removing a target product X in the form of fine crystals from a liquid phase P comprising the target product X and constituents other than the target product X by cooling suspension crystallization in the secondary chamber, into which the liquid phase P flows continuously, of an indirect heat exchanger with simultaneous continuous flow of a coolant through the primary chamber of the indirect heat exchanger and continuous withdrawal of a crystal suspension S having a degree of crystallization Y from the secondary chamber, in which the degree of crystallization Y is adjusted on the basis of a heat balance conducted continuously with the aid of a process computer.

31 Claims, 1 Drawing Sheet

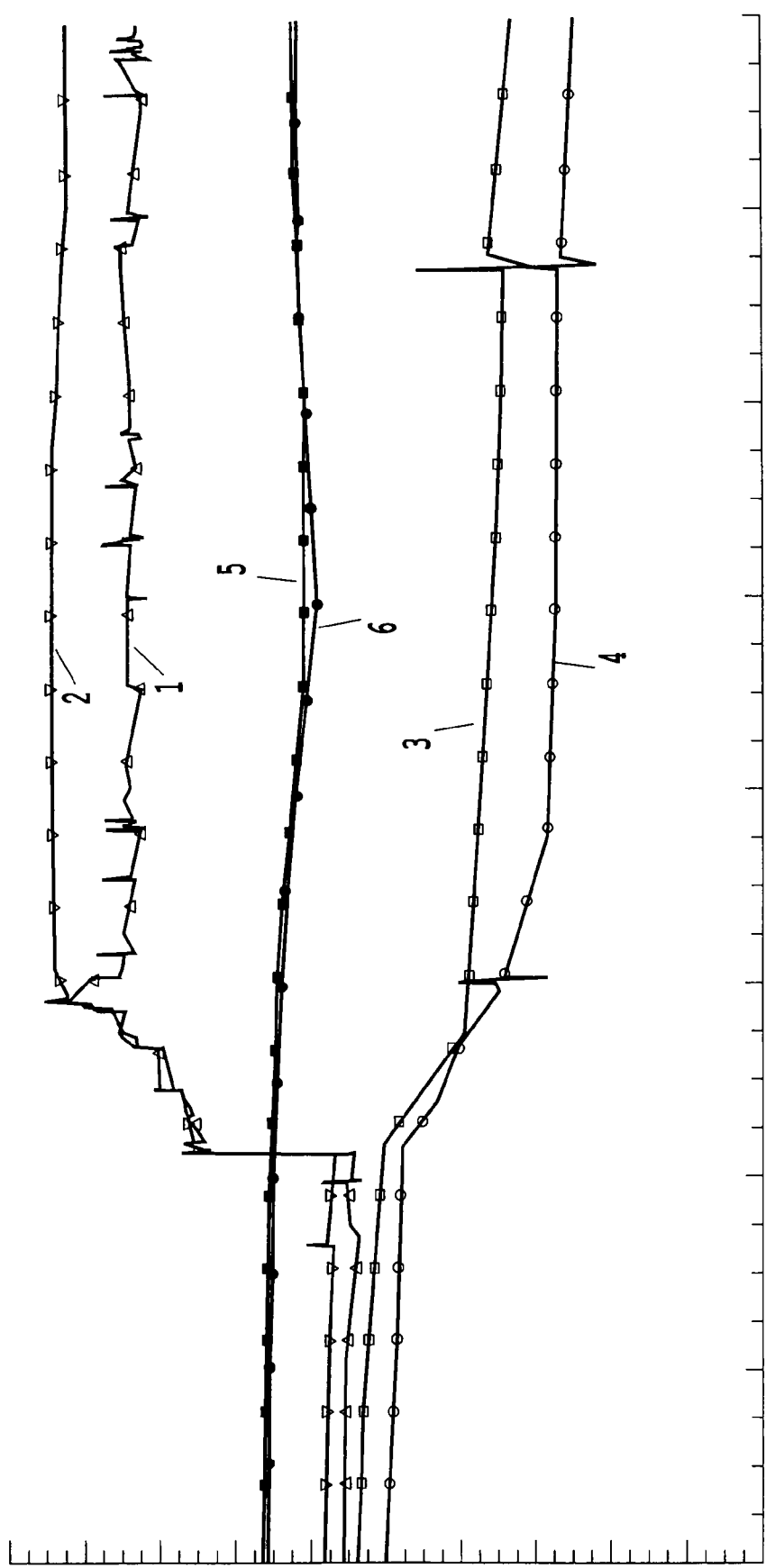

PROCESS FOR CONTINUOUSLY REMOVING A TARGET PRODUCT X IN THE FORM OF FINE CRYSTALS

The present invention relates to a process for continuously removing a target product X in the form of fine crystals of the target product X from a liquid phase P comprising the target product X and constituents other than the target product X with the aid of an (indirect) heat exchanger having a secondary chamber and at least one primary chamber, in which the secondary chamber and the at least one primary chamber are each spatially separated from one another by at least one material dividing wall which serves as an area for transferring heat out of the secondary chamber into the at least one primary chamber, in which liquid phase P is conducted continuously into the secondary chamber of the heat exchanger, while the at least one primary chamber is simultaneously flowed through by at least one fluid cooling medium such that fine crystals of the target product X are formed from the liquid phase P in the secondary chamber to leave a liquid residual phase R and are suspended in the remaining liquid residual phase R which, compared to the liquid phase P, comprises the constituents other than the target product X in enriched form and whose content of target product X is at least 70% by weight (based on the total weight of the liquid residual phase R) to obtain a suspension S of fine crystals of the target product X in the liquid residual phase R which has a degree of crystallization Y, and (crystal) suspension S is conducted continuously out of the secondary chamber of the heat exchanger.

The above-described processes for continuously removing a target product X in the form of fine crystals from a liquid phase P comprising the target product X and constituents other than the target product X with the aid of a heat exchanger (cooler or crystallizer) having a secondary chamber and at least one primary chamber are known (cf., for example, DE-A 103 32 758, WO 2004/035514, Research Disclosure Database Number 496005 and 479008, and German application 102007004960.0).

By virtue of the transfer of heat from liquid phase P supplied to the secondary chamber through the material dividing wall (the heat transfer area) which divides the secondary chamber and the at least one primary chamber into the coolant flowing in the at least one primary chamber, the liquid phase P cools until the saturation limit of liquid phase P with target product X is exceeded and oversaturation is counteracted by formation of crystals of the target product X.

The term "degree of crystallization Y" of the (crystal) suspension S comprising fine target product crystals suspended in the liquid residual phase R in this document means the mass fraction or else proportion by mass of the fine crystals present in the suspension S in the total mass of the suspension S. The degree of crystallization Y is thus calculated as the fraction of the crystal mass $m_{Kr, Y}$ present in the suspension S at the degree of crystallization Y divided by the total mass $m_S$ of the suspension:

$$Y = \frac{m_{Kr,Y}}{m_S}.$$

The degree of crystallization Y of the suspension S is thus necessarily between 0 and 1. The value "0" would correspond to an exclusively liquid phase, and the value 1 would correspond to an exclusively solid phase (i.e., in both cases, a suspension would no longer be present).

A crystallizative removal of a target product X from a liquid phase P comprising the target product X and constituents other than the target product X is employed especially in order to remove the target product X from by-products formed in the course of its preparation. The target product X may already have been prepared directly by chemical reaction in the liquid phase.

Of course, the target product X may also have been prepared, for example, in the gas phase, from which the target product X is subsequently converted to the liquid phase, generally by condensative and/or absorptive measures, normally together with some secondary components which accompany the target product X in the gas phase.

The crystallizative removal of the target product X can now be effected as a "sharp" thermal separating process, in principle, directly from the liquid phase which is obtained as described in the course of preparation of target product X and comprises the target product X and secondary components.

Frequently, however, the aforementioned liquid phase, before the use of a crystallizative removal of the target product X, will first be subjected to at least one "nonsharp" thermal separating process for the purpose of removing a portion of the aforementioned secondary components from the target product X.

A nonsharp separating process is defined as a separating process in which, from a thermodynamic point of view, the composition of the phase which forms when the separating process is employed and comprises target product X in enriched form is markedly dependent, in a thermodynamically necessary manner, on the composition of the mixture to be subjected to the separating process (cf., for example, McCabe-Thiele diagram). The nonsharp thermal separating processes include, for example, simple distillation, rectification, absorption, fractional condensation, desorption, extraction, stripping, azeotropic rectification, etc.

In contrast, crystallizative removal is a sharp thermal separating process in that the composition of the crystals which form, from a thermodynamic point of view, is very substantially independent of the composition of liquid starting mixture (see also DE-A 102005009890 and DE-A 10300816).

The reason for the advantage of the nonsharp separating processes is generally that they can be operated with high space-time yield. A disadvantage of nonsharp separating processes is, however, that the separating action achieved with them is comparatively restricted.

A disadvantage of sharp separating processes is their normally comparatively limited space-time yield, but normally with very high separating action.

Against the above background, the two separating principles are therefore frequently also employed in the following combination.

First, at least one nonsharp thermal separating process is applied to the product mixture obtained in the course of preparation of the target product X to obtain liquid phase P which already comprises the target product X, compared to its proportion by weight in the product mixture, in enriched form. This liquid phase P which, as well as the target product X, still comprises secondary components other than the target product X is subsequently subjected to a crystallizative removal of the target product X, and the liquid residual phase R which remains (which is frequently also referred to as mother liquor), which comprises the secondary components in comparatively enriched form, is recycled at least partly into at least one of the nonsharp thermal separating processes employed beforehand. In this way, the advantages of the two separating principles can be brought to bear simultaneously.

In many cases, a liquid phase P which comprises a target product X and is to be subjected to a crystallizative removal of the target product X (and this also applies to the liquid phases P relevant in this application) therefore comprises at least two, in many cases at least three or four, frequently at least five or six and often at least seven or eight, or at least nine or ten, secondary components other than the target product X (such secondary components are present in the liquid phase P in the context of this application when they are detectable as a constituent thereof, for example, by gas chromatography, liquid chromatography or other means (for example, such as water by Karl Fischer titration)).

In addition to by-products characteristic of the target product X according to its preparation, the liquid phase P comprising the target product X may also comprise solvent or solvent mixture and/or assistants (e.g. absorbants, extractants, etc.) used additionally in the course of for removal of the target product X from a reaction product mixture in the course of generation of liquid phase P. In other words, the liquid residual phase R may, for example, either be melts of the target product X and impurities or solutions of target product X and solvents (or solvent mixtures), and also generally impurities.

A process as described above for continuous crystallizative removal of a target product X from liquid phase P comprising the target product X and also secondary components (constituents) other than the target product X is typically followed by a continuous process for removing the crystals of the target product X present suspended in the liquid residual phase R in the (crystal) suspension S from the liquid residual phase R ("the mother liquor").

Such a removal can be undertaken, for example, by filtration, by screen centrifugation and/or in wash columns, as disclosed, for example, by WO 01/77056 and the prior art cited therein. Normally, such a removal also includes a wash of the crystals removed in order to remove mother liquor adhering on the crystal surface. Such a wash can be effected, for example, with the melt of crystals which have been removed and washed beforehand.

What is essential for an efficient (with regard both to the separating action and the space-time yield) continuous removal of the suspension crystals from remaining mother liquor (liquid residual phase R) is that the design of the separating apparatus used for the removal is adjusted to the degree of crystallization Y of the (crystal) suspension S, and Y remains very substantially stable during the continuous operation.

For example, the degree of crystallization Y of the suspension S influences all flow technology properties of the suspension S. However, it also influences, for example, the inner structure of the crystal cake to be washed or of the crystal bed to be washed and, as a result, also partly determines the washing action and the pressures which exist in the course of washing. In particular, the pressures, for example in the case of wash columns with forced transport as the given separating apparatus, in the case of an undesired rise in the degree of crystallization Y with otherwise identical mass flows, may rise steeply (for example exponentially) in unfavorable cases and cause either a safety shutdown or damage to the separating apparatus. The degree of crystallization Y, however, also influences the permeability of the crystal cake or crystal bed for the liquid residual phase R (the mother liquor remaining in the crystallizative removal). Moreover, in the case of small degrees of crystallization Y, when pusher centrifuges are used for crystal removal, there may be overshooting of the crystal suspension. In hydraulic wash columns, excessively low degrees of crystallization Y may cause the loss of the stable crystal bed.

Depending on the particular separating problem (including the separating apparatus used) and the crystal assembly, the ideal degree of crystallization Y is frequently in the range from 0.10 to 0.50, with greater frequency in the range from 0.20 to 0.40, and it is particularly frequently from 0.25 to 0.35 or 0.30.

In a continuous removal as described at the outset of a target product X in the form of fine crystals of the target product X from a liquid phase P comprising the target product X and constituents other than the target product X using a crystallization process as described at the outset of this document, it is therefore desirable that the degree of crystallization Y on which the design of the apparatus is based be kept very substantially constant over the operating time of the separating process.

Advantageously, the product of degree of crystallization Y with the number 100, over the operating time of the separating process, should deviate from the corresponding product of the target value desired for Y or of the steady-state value of Y by not more than ±5, preferably by not more than ±4, more preferably by not more than ±3 and most preferably by not more than ±2 or by not more than ±1.

In the known processes, the control parameter employed to adjust the degree of crystallization Y is typically the temperature of the suspension S conducted continuously out of the secondary chamber of the heat exchanger.

This is attributable to the fact that the temperature of a liquid phase comprising the target product X at which the formation of crystals of the target product X dissolved therein from this liquid phase sets in (neglecting the possibility of occurrence of supersaturation phenomena) is dependent upon the molar total number of compounds other than the target product X present additionally (in each case in dissolved form) in the liquid phase relative to the molar amount of target product X present therein.

The greater the aforementioned relative molar total number is, the lower the aforementioned crystallization onset temperature (or crystal formation temperature). In the literature, this phenomenon is also referred to as molar "crystallization point depression".

Since, however, the relative molar total number of compounds present (in dissolved form) in the liquid residual phase R other than the target product X still present in dissolved form in the liquid residual phase in each case necessarily increases with increasing degree of crystallization Y, the higher the degree of crystallization Y of the (crystal) suspension S withdrawn from the secondary chamber of the heat exchanger, the lower its temperature $T_S^{out}$.

In the case of a liquid phase P fed continuously to the secondary chamber of the heat exchanger with unchanged composition over the operating time, the temperature of the suspension S withdrawn from the secondary chamber is thus a direct measure of the degree of crystallization Y of the suspension S (especially owing to the large total surface area of the crystals present in the suspension S and the mixing (suspension) normally brought about in the secondary chamber of the heat exchanger, the suspension S, when withdrawn from the secondary chamber of the heat exchanger, is typically substantially in the state of equilibrium).

$T_S^{out}$ can be monitored (determined) continuously, for example, with the aid of a resistance thermometer immersed into the suspension S at the point of withdrawal of the suspension S from the secondary chamber. In the case that $T_S^{out}$ deviates from its target value corresponding to the desired degree of crystallization Y, for example, the temperature of the fluid cooling medium ($T_K^{in}$) fed to the primary chamber, as the control parameter, counteracting the aforementioned deviation, is raised or lowered as required.

One disadvantage of this closed-loop control structure for the degree of crystallization Y is, however, that it exclusively acts retrospectively. In other words, only when disruption to or a change in the steady operating state becomes perceptible in a changing $T_S^{out}$ and has thus already brought about a changed degree of crystallization Y does the system begin to return it to its target value (its steady-state value).

A further disadvantage of the above-described closed-loop control structure is that, with a decreasing proportion of the constituents other than the target product X present in the suspension S conducted out of the secondary chamber of the heat exchanger in the liquid residual phase, the dependence of the temperature $T_S^{out}$ on the degree of crystallization Y becomes flatter. This is disadvantageous especially in that the content in the liquid phase P of constituents other than the target product X, even in the steady operating state, can be subject to certain variations (this is especially true when at least one nonsharp separating process is involved in the preparation of liquid phase P). When these constituents are substances having a comparatively low molecular weight (e.g. $H_2O$), a comparatively minor variation in the proportion by weight of these constituents in many cases corresponds even to such variations in their molar proportion that these variations affect the particular current value of $T_S^{out}$ in the case of a real, possibly unchanged degree of crystallization Y, as if the degree of crystallization Y were changed perceptibly owing to disruption to or a change in the steady-state operation.

As a consequence, this induces a change in $T_K^{in}$, with which the closed-loop control system aims to return $T_S^{out}$ to its target value and, in doing so, undesirably induces a movement of the degree of crystallization Y away from its intended target value.

The disadvantages of the closed-loop control structure indicated, which have been described for illustrative purposes, grow to be serious especially when, for example, owing to a change in market demand for target product X, the stream of liquid phase P to be supplied to the secondary chamber of the heat exchanger has to be adjusted to the change in market demand.

In many cases, the market demand for a target product X (for example for an organic target compound such as acrylic acid, methacrylic acid, p-xylene or N-vinylpyrrolidone) is not a stable parameter but rather fluctuates over prolonged periods. For example, it can rise abruptly. Instead of reacting to such a rise in market demand with an additional production plant, it is also possible to react to it with an increase in the space-time yield of target product X in already existing production plants. Conversely, in the event that the market demand for target product X declines again, the space-time yield of target products X in the same production plant must be lowered again.

Such a transition from a steady operating state to another steady operating state, in the case of a crystallizative removal of the target product X from the liquid phase P comprising it as described at the outset of this document, is possible, for example, by raising or lowering the stream of liquid phase P to be fed to the secondary chamber of the heat exchanger according to an increasing or decreasing market demand for target product X, and simultaneously adjusting the flow of the at least one fluid cooling medium through the at least one primary chamber of the heat exchanger, such that a stream of crystal suspension S increased or reduced according to the change in market demand can be conducted out of the secondary chamber of the heat exchanger. Retention of the degree of crystallization Y of the suspension both during the transition to the new steady operating state and in this new steady operating state is advantageous for the reasons already detailed in this document in this case too.

However, a closed-loop control structure with sole use of $T_S^{out}$ as a control parameter for adjusting the degree of crystallization Y of the suspension S is manifestly unsuitable for a change in the operating state to be carried out as described.

One reason for this is that a change in the magnitude (in the intensity) of the stream of liquid phase P to be fed to the secondary chamber of the heat exchanger is generally accompanied by a changed spectrum of the constituents other than target product X present in the liquid phase P, and this change can relate both to the quantity of the individual constituents and their type. The cause of this fact is that the adjustment of the stream of liquid phase P must normally also be undertaken in existing production plants. However, such an adjustment typically necessarily entails changed reaction conditions in the preparation of the target product X (for example a changed reaction temperature, a changed loading of the catalyst bed with reaction gas mixture, a changed acidity of the reaction gas mixture, etc.), which generally both qualitatively and quantitatively affect the secondary component spectrum of the target product X to a certain degree and, in the further course of the overall preparation process, with the same degree of crystallization Y of the suspension S, can cause a possibly changed $T_S^{out}$. Otherwise, $T_S^{out}$ does not pick up a change in the magnitude of the stream of liquid phase P fed to the secondary chamber of the heat exchanger until this change has already brought about a change in the degree of crystallization Y. This fact would also be relevant if any other property (for example the viscosity, the electrical conductivity or an optical property) of the suspension S were to be employed as the sole control parameter for the adjustment of its degree of crystallization Y.

Against this background, it is an object of the present invention to provide an improved closed-loop control structure for the degree of crystallization Y in a process as described at the outset for crystallizative removal of a target product X, which still has the described disadvantages of a closed-loop control structure based only on $T_S^{out}$ to a reduced degree, if at all.

Accordingly, a process is provided for continuously removing a target product X in the form of fine crystals of the target product X from a liquid phase P comprising the target product X and constituents other than the target product X with the aid of an (indirect) heat exchanger having a secondary chamber and at least one primary chamber, in which the secondary chamber and the at least one primary chamber are each spatially separated from one another by at least one material (solid) dividing wall which serves as an area for transferring heat out of the secondary chamber into the at least one primary chamber, in which liquid phase P is conducted continuously into the secondary chamber of the heat exchanger, while the at least one primary chamber is simultaneously flowed through by at least one fluid cooling medium such that fine crystals of the target product X are formed from the liquid phase P in the secondary chamber to leave a liquid residual phase R and are suspended in the remaining liquid residual phase R which, compared to the liquid phase P, comprises the constituents other than the target product X in enriched form and whose content of target product X is at least 70% by weight to obtain a suspension S of fine crystals of the target product X in the liquid residual phase R which has a degree of crystallization Y, and suspension S is conducted continuously out of the secondary chamber of the heat exchanger, wherein the desired degree of crystallization Y of the suspension S conducted out of the secondary chamber of the heat exchanger is established by employing the difference, determined (or balanced out) at the particular operating time (in the course of a heat balance) with the aid of a process computer, between the flow of heat of crystallization $\dot{Q}_{Kr,Y}$ which develops in theoretical terms in the secondary chamber according to the degree of crystallization Y, and the difference formed between the heat flow $\dot{Q}_{out}$ otherwise conducted overall out of the secondary chamber of the heat exchanger and the heat flow $\dot{Q}_{in}$ otherwise conducted overall into the secondary chamber of the heat exchanger.

The process according to the invention is suitable especially when the content in the liquid residual phase R present in the suspension S withdrawn from the secondary chamber of target product X is ≧75% by weight, or ≧80% by weight, or ≧85% by weight, or ≧87% by weight, or ≧90% by weight, or ≧92% by weight, or ≧94% by weight, or ≧95% by weight, or ≧96% by weight, or ≧98% by weight, or ≧99% by weight. In general, the aforementioned content of target product X will, however, be ≦99.95% by weight, usually ≦99.9% by weight.

In other words, the process according to the invention is suitable in the case of those liquid phases P whose content of target product X is >70% by weight, or ≧75% by weight, or ≧80% by weight, or ≧85% by weight, or ≧87% by weight, or ≧90% by weight, or ≧92% by weight, or ≧94% by weight, or ≧95% by weight, or ≧96% by weight, or ≧98% by weight, or ≧99% by weight. In general, the aforementioned content in the liquid phase P fed to the secondary chamber of the heat exchanger in the process according to the invention of target product X will, however, be ≦99.995% by weight, usually ≦99.99% by weight.

The temperature with which the at least one fluid cooling medium is fed in the process according to the invention to the at least one primary chamber of the heat exchanger ($T_K^{in}$) is necessarily below that temperature with which the liquid phase P is fed simultaneously to the secondary chamber of the heat exchanger. Moreover, $T_K^{in}$ is necessarily below the crystallization onset temperature.

Useful target products X for the suspension crystallization configured as a cooling crystallization in accordance with the invention are, for example, saturated or unsaturated carboxylic acids such as acetic acid, propionic acid, acrylic acid and methacrylic acid, or substituted aromatics (with, for example, halogens, methyl, carboxyl, hydroxyl and/or nitrogen groups (e.g. —NH$_2$) as substituents), such as p-xylene, cresol and chlorobenzene, or polycyclic aromatic compounds such as naphthalene and bisphenol A, or isocyanates such as TDI and MDI, or vinyl compounds such as N-vinylpyrrolidone, or formaldehyde oligomers such as trioxane, or inorganic salts such as sodium or potassium salts (e.g. the sulfates, chlorides, bromides and iodides).

In particular, the process according to the invention is suitable in the case of acrylic acid, methacrylic acid, p-xylene or N-vinylpyrrolidone as the target product X, since a significant proportion of the by-products obtained in the course of their production has a lower molecular weight than the particular target product X itself.

The process according to the invention is very particularly suitable in the case of acrylic acid as the target product X and of crude acrylic acid as liquid phase P which has, for example, the following contents:

>70% by weight of acrylic acid,
up to 15% by weight of acetic acid,
up to 5% by weight of propionic acid,
up to 5% by weight of low molecular weight aldehydes,
up to 3% by weight of polymerization inhibitors, and
0 up to 5% by weight of diacrylic acid (Michael adduct), and
up to 25% by weight of water;

or

≧80% by weight of acrylic acid,
≧100 ppm by weight to ≦15% by weight of acetic acid,
≧10 ppm by weight to ≦5% by weight of propionic acid,
up to 5% by weight of low molecular weight aldehydes,
up to 3% by weight of polymerization inhibitors and
0 to 5% by weight of diacrylic acid (Michael adduct), and
up to 15% by weight of water;

or

≧85% by weight of acrylic acid,
≧100 ppm by weight to ≦10% by weight of acetic acid,
≧10 ppm by weight to ≦5% by weight of propionic acid,
up to 5% by weight of low molecular weight aldehydes,
up to 3% by weight of polymerization inhibitors,
0 to 5% by weight of diacrylic acid (Michael adduct), and
up to 10% by weight of water;

or

≧90% by weight of acrylic acid,
≧100 ppm by weight to ≦5% by weight of acetic acid,
≧10 ppm by weight to ≦2% by weight of propionic acid,
up to 2% by weight of low molecular weight aldehydes,
up to 2% by weight of polymerization inhibitors,
0 to 3% by weight of diacrylic acid (Michael adduct), and
up to 9% by weight of water;

or

≧95% by weight of acrylic acid,
≧100 ppm by weight to ≦3% by weight of acetic acid,
≧10 ppm by weight to ≦2% by weight of propionic acid,
up to 2% by weight of low molecular weight aldehydes,
up to 2% by weight of polymerization inhibitors,
0 to 2% by weight of diacrylic acid (Michael adduct), and
up to 4.9% by weight of water;

or 93 to 98% by weight of acrylic acid,
1 to 5% by weight of water,
0.001 to 3% by weight of acrolein,
≧0 to 3% by weight of methacrolein,
≧0 to 3% by weight of methacrylic acid,
0.1 to 3% by weight of acetic acid,
0.01 to 3% by weight of propionic acid,
0.001 to 3% by weight of formaldehyde,
0.001 to 3% by weight of aldehydes other than formaldehyde,
0.01 to 3% by weight of maleic acid, and
≧0 to 3% by weight of protoanemonin.

Such crude acrylic acids are obtainable, for example, by the known prior art processes (cf., for example, WO 01/77056, DE-A 103 32 758, DE-A 102 43 625, German application 10 2006 057 631.4, German application 10 2006 062 258.8, German application 10 2007 004 960.0, WO 2004/035514, German application 10 2006 049 939.5, DE-A 10 2005 029 629, WO 03/041832 and DE-A 10 2005 015 639 and also the prior art cited in these documents).

These are generally crude acrylic acids which are obtained (derived) from the product gas mixture of a heterogeneously catalyzed partial oxidation of at least one C$_3$ precursor compound of acrylic acid (e.g. propane, propylene, glycerol, acrolein, propionic acid, propanol and/or propionaldehyde).

For the process according to the invention, useful liquid phases P include especially such crude acrylic acid which has been obtained from the product gas mixture of a heterogeneously catalyzed partial gas phase oxidation of at least one $C_3$ precursor compound using at least one nonsharp separating process. This is especially true when the acrylic acid crystals present suspended in the liquid residual phase R in the suspension S obtained when the process according to the invention is applied to such a crude acrylic acid as liquid phase P is subsequently removed from the liquid residual phase R, and the remaining residual phase R is recycled at least partly into at least one nonsharp separating process used to prepare the crude acrylic acid from the product gas mixture of the gas phase partial oxidation.

The basic structure of such a combined use of nonsharp separating processes and the sharp separating process of crystallization is taught, for example, by DE-A 196 06 877, EP-A 792 867, and also EP-A 1 4843 08, EP-A 1 116 709 and especially EP-A 1 015 410.

In general, the at least one nonsharp separating process employed to obtain the liquid phase P to be treated in accordance with the invention from the product gas mixture of a heterogeneously catalyzed partial gas phase oxidation of at least one $C_3$ precursor compound of acrylic acid will be a distillation, rectification, absorption, adsorption, extraction, desorption, stripping, distraction, (partial) condensation, fractional condensation, a membrane separating process such as a pervaporation/vapor permeation, or a combination of such processes.

In the simplest case, the crude acrylic acid to be used as the liquid phase P in the process according to the invention may be the absorbate and/or partial condensate and/or condensate obtained by fractionation from an absorptive and/or condensative removal of acrylic acid from the product gas mixture of a heterogeneously catalyzed partial gas phase oxidation of at least one of the $C_3$ precursors listed in this document. The liquid residual phase R (mother liquor) removed from the suspension S is then appropriately recycled into the absorption and/or condensation.

Appropriately, a combination of nonsharp and sharp (crystallizative) removal of the acrylic acid from the product gas mixture of the gas phase partial oxidation to be employed as described has at least one outlet for secondary components other than acrylic acid which boil at a higher temperature than acrylic acid under standard pressure (1 bar). Advantageously in application terms, this is on the side of the nonsharp separating processes. In general, the outlet of this type used will be the bottoms liquid of a separating column, from which separating column liquid phase P (the crude acrylic acid to be used as such) itself or the stream to be converted later to the liquid phase P (the crude acrylic acid to be used as such) is withdrawn, for example, via a side draw and/or via a top draw. Of course, such an outlet may also be on the side of the inventive crystallizative removal. In this case, the outlet may consist of liquid residual phase R (mother liquor). Typically, there is additionally an outlet for secondary components which boil at a lower temperature than acrylic acid at standard pressure on the side of the nonsharp separating processes.

Advantageously, the acrylic acid to be used as the liquid phase P in the process according to the invention is based on a partial oxidation product gas mixture which comprises:
1 to 30% by volume of acrylic acid,
$\geq 0$ to or 0.005 to 10% by volume of propylene,
$\geq 0$ or 0.001 to 2% by volume of acrolein,
$\geq 0$ or 0.001 to 2% by volume of methacrolein,
$\geq 0$ or 0.001 to 2% by volume of methacrylic acid,
$\geq 0$ or 0.005 to 10% by volume of molecular oxygen,
$\geq 0$ or 0.005 to 3% by volume of acetic acid,
$\geq 0$ or 0.001 to 2% by volume of propionic acid,
$\geq 0$ or 0.001 to 2% by volume of formaldehyde,
$\geq 0$ or 0.001 to 2% by volume of other aldehydes,
and 10 to 98 or 50 to 98% by volume of (inert) diluent gases.

The diluent gases may, for example, comprise:
$\geq 0$ or 0.005 to 90% by volume of saturated $C_1$-$C_6$-hydrocarbons (especially propane, methane and/or ethane),
$\geq 0$ or 0.05 to 30% by volume of steam,
$\geq 0$ or 0.05 to 15% by volume of carbon oxides (CO and/or $CO_2$),
and $\geq 0$ or 1 to 90% by volume of molecular nitrogen.

The partial oxidation product gas mixture may be derived especially from a partial oxidation as described in documents EP-A 1 818 324, DE-A 10 2004 032 129 and their equivalent foreign patents, DE-A 102 45 585, WO 03/076370, WO 01/96271, EP-A 117 146, WO 03/011804, U.S. Pat. No. 3,161,670, DE-A 33 135 73, DE-A 103 16 039 and WO 01/96270, proceeding from propylene and/or propane, and, as a propylene source, may have a propane dehydrogenation and/or oxydehydrogenation (if appropriate under heterogeneous catalysis) as a preceding reaction stage.

Advantageously, the crude acrylic acid desired as the liquid phase P to be treated in accordance with the invention will be obtained from the aforementioned product gas mixtures of the $C_3$ acrylic acid precursor partial oxidation by condensing acrylic acid out of the product gas mixture of the partial oxidation. The condensate obtained advantageously directly forms liquid phase P to be treated in accordance with the invention. Advantageously, the acrylic acid is condensed out of the product gas mixture (which has been cooled beforehand if appropriate) as a fractional condensation (on which is additionally superimposed, if appropriate, an absorption with water and/or aqueous solution (it generally comprises $\geq 90\%$ by weight, frequently $\geq 95\%$ by weight, of water), in order to reduce acrylic acid losses; cf., for example, EP-A 1 818 324), as described in detail, for example, in documents EP-A 1 015 410, WO 2004/035514, DE-A 102 43 625, EP-A 1 015 411, DE-A 102 35 847, EP-A 1 159 249, EP-A 1 163 201, EP-A 1 066 239 and EP-A 920 408.

In this case, the product gas mixture is appropriately, if appropriate on completion of direct and/or indirect cooling (for example with a quench liquid according to EP-A 1 066 239, or according to EP-A 1 163 201), fractionally condensed in a separating column having separating internals, ascending into itself, with side draw removal of crude acrylic acid (which preferably forms the liquid phase P to be treated in accordance with the invention; if appropriate, the crude acrylic acid is treated by rectification and/or distillation to obtain the liquid phase P).

Fine acrylic acid crystals can then be removed in accordance with the invention from liquid phase P obtained by condensation (and if appropriate additionally by rectification). Mother liquor (residual phase R) removed subsequently from the suspension S obtainable will, according to the model, for example, of EP-A 920 408 or WO 2004/035514, be recycled at least partly, preferably completely, into the condensation of the acrylic acid out of the product gas mixture. The high boiler outlet will be sited below the side draw of the crude acrylic acid.

Liquid phase P (crude acrylic acid) which has been obtained in this way by partial or total condensation and/or superimposed absorption with water or aqueous solution and if appropriate rectificative aftertreatment and can be treated in accordance with the invention may comprise:
$\geq 85$ to 99.5% by weight of acrylic acid,
$\geq 0$, generally 0.1 to 40% by weight of water,
$\geq 0$, generally 0.001 to 5% by weight of acrolein,
$\geq 0$, in some cases 0.001 to 10% by weight of methacrolein, ≧0, in some cases 0.001 to 10% by weight of methacrylic acid,
≧0, generally 0.01 to 10 or to 5% by weight of acetic acid,
≧0, generally 0.01 to 5% by weight of propionic acid,
≧0, generally 0.001 to 5% by weight of formaldehyde,
≧0, generally 0.001 to 5% by weight of aldehydes other than formaldehyde (per aldehyde),
≧0, generally 0.01 to 5% by weight of maleic acid,
≧0, generally 0.01 to 10% by weight of benzaldehyde and/or benzoic acid, and
≧0 to 3% by weight of protoanemonin.

For the separation of suspension S into crystals present therein and liquid residual phase R (mother liquor), all processes detailed in documents WO 01/77856, WO 02/055469 and WO 03/078378 for separating suspension crystals and mother liquor are useful (for example mechanical separating processes such as centrifugation). Preference is given to separation in a wash column. Advantageously, this is a wash column with forced transport of the deposited acrylic acid crystals. The proportion by volume of crystals in the crystal bed generally reaches values of >0.5. In general, the wash column is operated at values of from 0.6 to 0.75. The wash liquid used is advantageously the melt of acrylic acid crystals purified (removed) beforehand in the wash column. The wash is normally effected in countercurrent. The process according to the invention thus especially comprises processes which comprise the following process steps (these processes are also employable in this way in the case of target products other than acrylic acid):
a) inventive crystallizative removal of acrylic acid from a liquid phase P (for example from liquid crude acrylic acid) with formation (withdrawal) of a suspension S,
b) separating the suspension S into acrylic acid crystals and mother liquor (liquid residual phase R),
c) at least partly melting the acrylic acid crystals removed and
d) at least partly recycling the molten acrylic acid crystals to step b) and/or to step a).

Step b) is preferably effected by countercurrent washing with molten acrylic acid crystals removed beforehand recycled in step b). Advantageously, steps b), c) and d) are effected in a wash column.

Advantageously in accordance with the invention, the liquid phase P (in the case of acrylic acid as target product X), when the process according to the invention is employed, comprises water, since formation of acrylic acid crystals in the presence of water, according to the teaching of WO 01/77056 and WO 03/078378, causes a particularly favorable crystal form for the subsequent separation of the crystals from remaining mother liquor. This is especially true when the subsequent mother liquor removal from the suspension S is performed in a wash column, and even more true when the wash liquid used is the melt of acrylic acid crystals already purified in (removed in a purifying manner from) the wash column.

In other words, the process according to the invention comprises especially processes in which the crude acrylic acid as the liquid phase P is converted in accordance with the invention to a suspension S consisting of acrylic acid crystals and liquid residual phase R (mother liquor), a portion of the remaining mother liquor is, if appropriate, removed mechanically from the suspension S, and the acrylic acid crystals are freed of remaining mother liquor in a wash column, with the proviso that
a) the liquid phase P (the crude acrylic acid), based on the acrylic acid present therein, comprises from 0.20 to 30, frequently to 20, often to 10% by weight of water, and
b) the wash liquid used is the melt of acrylic acid crystals purified in (removed in a purifying manner from) the wash column.

In particular, the process according to the invention comprises the above processes, wherein the liquid phase P comprises >70% by weight of acrylic acid, or ≧75% by weight of acrylic acid, or ≧80% by weight of acrylic acid, or ≧85% by weight of acrylic acid, or ≧90% by weight of acrylic acid, or ≧95% by weight of acrylic acid.

Moreover, it is advantageous in accordance with the invention when the water content of the liquid phase P (of the crude acrylic acid) in the above-described procedures (or quite generally when the process according to the invention is employed) with acrylic acid as the target product X, based on acrylic acid present in the liquid phase P, is from 0.2 or 0.4 to 8, or to 10, or to 20, or to 30% by weight, or from 0.6 to 5% by weight, or from 0.60 to 3% by weight.

Of course, the process according to the invention can also be applied to all crude acrylic acids of WO 98/01414, and to all crude p-xylenes of EP-A 097405.

In general, $T_S^{out}$ in the case of use of crude acrylic acid as the liquid phase P in the process according to the invention (acrylic acid being the inventive target product X) is in the range from −25° C. to +14° C., especially in the range from −5° C. to +12° C. and particularly advantageously in the range from 4 or 6 to 9° C.

All of the aforementioned is true in particular when the wash column is a wash column with forced transport of the acrylic acid crystals, and in particular when it is a hydraulic or mechanical wash column according to WO 01/77056 and is operated as stated there.

All of the aforementioned is true in particular when the wash column is configured and is operated according to the teachings of WO 03/041832 and of WO 03/041833 and WO 2006/111565.

The process according to the invention thus permits, with the sequence of "partial oxidation of at least one $C_3$ precursor compound, fractional acrylic acid condensation and/or (e.g. aqueous) absorption from the product gas mixture of the partial oxidation, inventive crystallizative removal of acrylic acid from the acrylic acid condensate withdrawn as the liquid phase P from the acrylic acid condensation while conducting an acrylic acid crystal suspension S out of the secondary chamber of the heat exchanger, and separating the suspension S into remaining mother liquor and pure acrylic acid crystals in a wash column using a melt of pure acrylic acid crystals removed beforehand as the wash liquid", in a highly efficient manner, the preparation of superabsorbent-grade acrylic acid adjusted to the particular market demand.

Of course, all process steps in which acrylic acid is involved are performed with inhibition of polymerization. The procedure may be as described in the prior art. A prominent position among the entirety of the available acrylic acid process stabilizers is taken by dibenzo-1,4-thiazine (PTZ), 4-hydroxy-2,2,6,6-tetramethylpiperidine 1-oxyl (4-OH-TEMPO) and p-methoxyphenol (MEHQ), which may each be part of the liquid phase P (of the crude acrylic acid) alone, in pairs or as a three-substance mixture. Typically, their total amount based on acrylic acid present in the liquid phase P is from 0.001 to 2% by weight.

In a corresponding manner to that outlined in an illustrative manner for acrylic acid, the process according to the invention can also be integrated into the preparation of other target products X.

In other words, the present application comprises, in particular, a process in which the process according to the invention is followed by a process for continuously removing fine crystals of the target product X present in the suspension S, in which the suspension S is fed to a wash column which has a wash column wall which surrounds a process chamber, mother liquor (liquid residual phase R) is released from the process chamber while retaining the crystals present in the suspension S to form a crystal bed in the process chamber from the suspension S conducted into the process chamber by means of filter equipment, the crystal bed is conveyed within the process chamber, at least one force other than gravity acts in the process chamber in the conveying direction of the crystal bed and conveys the crystal bed within the process chamber, pure melt which consists of molten crystals which have been removed beforehand by this wash column separation process is conducted within the process chamber in countercurrent to the crystal bed such that a wash front which divides the crystal bed into a mother liquor zone and into a pure melt zone forms in the crystal bed, and crystals in solid and/or molten form which have been washed in the wash column are discharged continuously at the opposite end of the wash column to the feed of the suspension S.

The aforementioned is true in particular when the target product X in the process according to the invention is acrylic acid (especially when the liquid phase P is crude acrylic acid according to this document). In general, in this case, the removal of the fine acrylic acid crystals is followed by a further process in which acrylic acid crystals removed are melted and then subjected to a polymerization (preferably a free-radical polymerization) with themselves or with other at least monoethylenically unsaturated compounds (for example to a solution polymerization, emulsion polymerization, suspension polymerization, gas phase polymerization, or bulk polymerization). Such a process may also follow when the separation of crystals and mother liquor is undertaken in a different manner than with a wash column.

The aforementioned wash column is advantageously a hydraulic wash column or a mechanical wash column. Descriptions of corresponding wash columns can be found, for example, in WO 2006/111565, in DE-A 10 2007 032 633, in WO 03/041832, in WO 03/041833, in DE-A 10 2005 015 639 and in WO 01/77056, and the prior art cited in these documents.

The flow of heat of crystallization $\dot{Q}_{Kr,Y}$ which evolves in theoretical terms according to the desired degree of crystallization Y in the secondary chamber of the heat exchanger (cooler) is understood in this document to mean that heat of crystallization (crystallization enthalpy) released overall per unit time in the secondary chamber as a result of the crystallization of the target product X that would evolve at any time in the secondary chamber of the heat exchanger if the mass flow $\dot{m}_P$ of liquid phase P supplied to it at the current time were to be a steady-state mass flow which were to be converted to a steady-state crystal suspension S within the secondary chamber and were to be conducted as such out of the secondary chamber as the steady-state mass flow $\dot{m}_S = \dot{m}_P$ with the steady-state degree of crystallization Y.

In the inventive closed-loop control structure, $\dot{Q}_{Kr,Y}$ forms the guide parameter which is fed (supplied) from outside to the closed-loop control circuit at any time.

To this end, $\dot{Q}_{Kr,Y}$ is calculated as follows:

$$\dot{Q}_{Kr,Y} = \dot{m}_P \cdot Y \cdot c_{Kr} \qquad \text{(relationship 1).}$$

$\dot{m}_P$ is the mass flow of liquid phase P fed in each case at the present time to the secondary chamber of the heat exchanger (frequently, $\dot{m}_P$ is also referred to as the mass flow intensity).

$\dot{m}_P$ is, for example, determinable continuously with the aid of a coriolis mass flow meter. This is in principle a tube, for example a metallic tube, which may, for example, have the shape of an arc and is flowed through by the liquid phase P in direct flow. For example, the pipe arc is set in vibration by means of a magnet. On the inlet and outlet side, magnets are mounted on the vibration system, which induce a voltage proportional to motion in an adjoining coil in each case.

The signals thus generated are sinusoidal. Without mass flow, the two signals are in phase. In the event of mass flow, caused by the coriolis force acting on the flowing mass owing to the marked vibration, there is a phase shift of the two aforementioned signals, the phase angle offset being a measure of the mass flow (or of the mass flow intensity). Since the resonance frequency of the vibrating overall system, as well as the properties of the measurement tube, is dependent on the mass density of the measurement tube contents, the vibration frequency in the event of mass flow correlates directly with the mass density of the mass flow flowing through the measurement tube, which is why determination of the mass density of the flowing mass flow is possible with a coriolis mass flow meter simultaneously to the determination of the mass flow. The two determinations are also possible when the mass flow is polyphasic, i.e., for example, a crystal suspension.

Alternatively, the current mass flow $\dot{m}_P$ can also be determined with the aid of a vortex flow meter. In this measurement method, a perturbation body is installed into the flow channel of the mass flow. At the perturbation body toward which the mass flow flows, vortices form alternately on the two sides, which are removed by the flow and entrained with it, and form a Karman vortex street beyond the perturbation body in flow direction. The frequency of the vortex removal correlates (irrespective of mass density and viscosity of the mass flow) directly with the flow rate of the mass flow to be determined (there is generally direct proportionality). The local pressure changes accompanying the vortex removal are detected by a piezo sensor and converted to electrical pulses corresponding to the vortex frequency. Taking account of the mass density of liquid phase P and of the flow cross section, the measurement result forms a direct measure for the mass flow.

A further means of obtaining the mass flow $\dot{m}_P$ is offered by magnetic inductive flow meters. These are precision measuring equipment for measuring the volume flow of liquids which have electrical conductivity, as is the case, for example, in crude acrylic acid as liquid phase P. The measurement principle exploits the action of force on charges moving in a magnetic field (see Hall effect).

The liquid phase P to be analyzed flows through a tube made of non-magnetic material. Charge carriers (positive/negative) present therein are deflected by a magnetic field lying at right angles to the flow direction and generate electrical voltages in the millivolt range at electrodes in the pipe wall. The coupling may be either by means of electrical connection or capacitance. Since the magnetic induction B (the magnetic field strength) and the electrode separation are constant values, the measured voltage is proportional to the flow rate. Multiplication by the cross-sectional area of the flow meter and by the mass density of the mass flow gives rise to the desired mass flow (or the desired mass flow intensity).

In the predominant number of processes for preparing liquid phases P to be treated in accordance with the invention, the mass density of liquid phase P, based on that window within which the composition of liquid phase P may vary over the operating time, is comparatively robust. In other words, with regard to variations in composition, the mass density in these cases can be given as a constant in the context of the inventive closed-loop control structure. With regard to that temperature with which the liquid phase P is fed to the secondary chamber of the heat exchanger ($T_P^{in}$), this is frequently no longer the case. Since $T_P^{in}$ is amenable in a comparatively simple manner to a continuous determination with the aid of thermal elements or resistance thermometers, one can be carried out for these cases and then processed with the temperature dependence, recorded in the process computer (having been determined experimentally beforehand), of the mass density of the relevant liquid phase P relative to the current mass density of liquid phase P conducted into the secondary chamber of the heat exchanger, which results, with the aid of the volume flows to be determined as described above, in the mass flow $\dot{m}_P$ required for relationship 1.

Alternatively, the mass density of the liquid phase P fed to the secondary chamber of the heat exchanger can also additionally be determined continuously with the aid of a flexural vibrator. In these cases, the flexural vibrator is used in addition to one of the measurement apparatus described above for the volume flow of liquid phase P fed to the secondary chamber in the bypass to the actual mass flow. In a flexural vibrator, the determination of the density of liquids is derived from an electronic measurement of the vibration time (or vibration frequency), which, as already stated in connection with the coriolis mass flow meter, correlates directly with this density.

This is because, when a sample to be analyzed is introduced into a vibratory structure, its intrinsic frequency is influenced by the mass of the sample introduced. The vibratory structure is preferably a hollow flexural vibrator made, for example, of glass or metal and bent into a U-shape, which is induced to vibrate without damping by an electronic method. The two legs of the U-shaped vibratory tube form the spring elements of the vibrator ("the tuning forks"). The direction of vibration is normally in the plane of the two legs. The intrinsic frequency of the vibrator is influenced only by that part of the sample which is actually involved in the vibration. This volume involved in the vibration is limited by the vibration nodes at rest at the clamping sites of the vibrator. When the vibrator is filled with the sample at least up to the clamping sites, it is always the same, exactly defined volume that is involved in the vibration, and the mass of the sample can therefore be assumed to be proportional to its density. Overfilling of the vibrator above and beyond the clamping sites is unimportant for the measurement. For this reason, it is also possible with the vibrator to measure densities of media which flow through the vibrator (continuous measurement).

Further methods of flow measurement suitable for the process according to the invention can be found, for example, in "Technische Durchflussmessung" [Industrial Flow Measurement], editor: K. W. Bonfig, 3rd edition, 2002, Vulkan Verlag Essen. These further flow measurement methods also include variable area flow measurement. A variable area flow meter consists, for example, of a vertical tube which widens in the upward direction and is made, for example, of glass or nonmagnetic metal, which is flowed through by the fluid from the bottom upward. In the tubes, for example glass tubes, is disposed a mobile floating body. This has a flow resistance in the flowing fluid, i.e. a force Fr acts on it in the direction of flow, which is dependent on the flow rate. This is counteracted by the gravity $F_G$ on the floating body.

The height of the floating body in the variable area flow meter depends on the volume flow. In the case of a rising volume flow, the flow resistance increases. The floating body rises and the area between floating body and the glass tube becomes greater. At the same time, the flow resistance falls again until it is equal to the gravity of the floating body and the body floats. The floating height of the floating body in the glass tube is thus a direct measure for the particular flow rate of the fluid. For example, with the aid of a small magnet incorporated into the floating body, which is capable of interacting with a second magnet mounted in a mobile manner in the environment of the glass tube, the height of the floating body is communicated outward and converted to an electromagnetic signal.

Sensors which work by the measurement principles described in this document are commercially available.

The degree of crystallization is defined as desired (according to the design) by the operator, and $C_{Kr}$ is essentially a substance property which is characteristic of the target product X and, in the range of the working pressures typically employed for the process according to the invention (normally not more than 5 bar, usually not more than 3 bar, frequently not more than 2 bar and generally $\leq 1.5$ bar and $\geq 1$ bar; for reasons of, for example, monomers being sucked out, the working pressure may also be below atmospheric pressure), is independent thereof. This normally applies to the temperature dependence of $C_{Kr}$. The latter is especially true taking account of the fact that differences $T_P^{in} - T_S^{out} > 50$ K are relatively unusual for the process according to the invention. The constituents other than target product X present in liquid phase P normally influence $C_{Kr}$ only slightly.

However, anyone wishing to hit the desired absolute value of Y as exactly as possible (in many cases, however, the primary aim is a relatively constant Y over the operating time of the process according to the invention, limited deviations from the contemplated ideal absolute value for Y being acceptable) can determine $C_{Kr}$ (J/g) for a crystallizative removal of the target product X experimentally by corresponding caloric measurement from the liquid phase P, and then use this value for $C_{Kr}$ to calculate the heat flow $\dot{Q}_{K,Y}$, instead of using the substance value for $C_{Kr}$ which can be taken from the literature for this calculation (in this way, a slight influence of the possible secondary components present in liquid phase P is taken into account). $C_{Kr}$ is that amount of heat which is released when one gram of target product X crystallizes out.

The heat flow $\dot{Q}_{K,out}$ conducted at a particular operating time out of the secondary chamber to the fluid cooling medium (generally a cooling liquid) flowing through the at least one primary chamber through the at least one material dividing wall dividing the two chambers is, to a very good approximation, given by:

$$\dot{Q}_{K,out} = \dot{m}_K \cdot C_P^{K*}(T_K^{out} T_K^{in}) \qquad \text{(relationship 2)}.$$

In this relationship, $\dot{m}_K$ is that mass flow (or the mass flow intensity thereof) with which the coolant is fed to the at least one primary chamber and with which it necessarily also flows back out of it according to the law of conservation of mass. $\dot{m}_K$ can be determined experimentally and continuously (monitored online) using one of the measurement processes detailed in this document for $\dot{m}_P$.

$C_P^K$ is the mass-specific heat capacity (enthalpy) based on heating at constant pressure (J/(g·K)), that the cooling medium (coolant) has at the temperature $(T_K^{out} + T_K^{in})/2$, where $T_K^{out}$ is that temperature with which the coolant is conducted out of the at least one primary chamber, and $T_K^{in}$ is that temperature (in both cases in degrees Kelvin (as is also the case for all other temperature measurements and temperature considerations in this document, unless explicitly mentioned or stated otherwise)) with which the coolant is conducted into the at least one primary chamber.

$T_K^{out}$ and $T_K^{in}$ may, as detailed below, be determined experimentally online.

$C_P^K$ can be determined experimentally for the coolant used in each case as a function of temperature by corresponding caloric measurement (at the working pressure contemplated in the primary chamber), and recorded in the process computer as a function of temperature.

In many cases, especially in the case of use of cooling liquids, the temperature dependence of $C_P^K$ in the temperature range relevant in accordance with the invention (differences $T_K^{out}-T_K^{in} \gtrsim 50$ K are relatively unusual for the process according to the invention) is, however, negligible, as a result of which the calculation of $\dot{Q}_{K,out}$ is additionally simplified (a constant $C_P^K$ at a temperature representative for the process can then be recorded in the process computer). The pressure dependence of $C_P^K$ is negligible for the purposes of the invention.

It is not entirely unproblematic that, on the side of the at least one dividing wall dividing the primary chamber from the secondary chamber in each case which faces the secondary chamber, there may be formation of crystal layers which adhere on the dividing wall, which reduce the heat transfer through the dividing wall. For this reason, the side of such dividing walls facing the secondary chamber is in many cases operated with wipers. In other words, a driven wiping apparatus in the secondary chamber (for example analogously to windshield wipers of an automobile) continuously wipes away (continuously scratches off or away) crystals of the target product X adhering on the relevant side of the dividing wall and suspends them in the suspension S. At the same time, the wiping apparatus generally brings about mixing of the crystal suspension S in the secondary chamber.

In many cases, however, there remain dividing wall area elements which can be wiped only with difficulty, if at all. This is, for example, the case when the primary chamber is the interior of a circular cooling disk which, for example, is immersed in a simple manner into the liquid phase flowing in the secondary chamber. While the front side and the back side of the cooling disk are amenable to wiping in a comparatively simple manner, this is normally not the case for the outer area of the cooling disk. Such area elements are therefore generally subjected to trace heating, which is intended to suppress their incrustation with crystals. Such an incrustation is undesired not least because it may spontaneously become detached when it exceeds a certain degree and, in the form of resulting relatively large crystal lumps, might disrupt the crystallizative separating process.

As a result of the trace heating, a heat flow $\dot{Q}_{H,in}$ is supplied to the secondary chamber in balance terms (the proportion of the heat flow which flows directly into the at least one primary chamber as a result of the trace heating can be treated in terms of balance in the context of the present invention as if it were to flow into the primary chamber via the secondary chamber).

In the case of electrical resistance trace heating, this heat flow can be calculated from the electrical current J and the electrical resistance R ($\dot{Q}_{H,in}=I^2 \cdot R$). Of course, such trace heating can also be implemented by indirect heat exchange. For example, in the case of use of the circular cooling disks addressed above, it is possible to mount, on their outer area (to the unwiped disk wall end side), for example, a hollow heating tube (or another hollow profile), into which a fluid heating medium is supplied continuously with the temperature $T_H^{in}$ and out of which the same fluid heating medium is conducted again with the temperature $T_H^{out} < T_H^{in}$. The fluid heating medium is preferably likewise a liquid. More preferably, the heating medium is the same substance which is conducted through the primary chamber simultaneously as a coolant with another temperature.

In this case of trace heating by indirect heat exchange, entirely analogously to relationship 2, the following relationship 3 applies for $\dot{Q}_{H,in}$:

$$\dot{Q}_{H,in} = \dot{m}_H \cdot c_P^{H*} (T_H^{in} - T_H^{out}).$$

$\dot{m}_H$ is that mass flow (or the mass flow intensity thereof) with which the heating medium is fed to the heating tube and with which it necessarily flows back out of it according to the law of conservation of mass. $\dot{m}_H$ can be determined continuously and experimentally (monitored online) using one of the measurement processes detailed in this document for $\dot{m}_P$.

$C_P^H$ is the mass-specific heat capacity (enthalpy) based on heating at constant pressure (J/(g·K)) that the heating medium has at the temperature $(T_H^{in}+T_H^{out})/2$. In other words, it is that amount of heat which is required to heat 1 g of the heating medium which has the aforementioned temperature by 1 K at constant pressure. Otherwise, $C_P^H$ can be determined experimentally in a corresponding manner and should be considered in relationship 3 like $C_P^K$ in relationship 2.

The online determination of the relevant temperatures $T_H^{in}$, $T_H^{out}$, $T_K^{out}$, $T_K^{in}$ is possible in a simple manner, for example, with the aid of resistance thermometers. A resistance thermometer is a thermometer in which the temperature is not determined with reference to the change in length or volume of a substance but rather via the temperature dependence of the electrical resistance of substances. Pure metals exhibit greater changes in resistance than alloys and have a relatively constant temperature coefficient of electrical resistance. For the process according to the invention, preference is given to using noble metals (more preferably platinum), since they exhibit particularly low aging, and the resistance thermometers can be manufactured therefrom with low tolerances, which enables particularly precise temperature measurements. However, the resistance may in principle also consist of ceramic (sintered metal oxides) or semiconductors, which allow even higher sensitivities to be achieved. These resistances are referred to as thermistors, a distinction being drawn between hot conductors (NTC resistances) and cold conductors (PTC resistances). Particularly exact temperature detection is possible by virtue of the resistance thermometer used in each case, before its use, being calibrated once again specifically to the contemplated use temperature range. In general, the metal on which the resistance thermometer is based is not conducted into the medium to be measured as such, but rather disposed in a corresponding measurement sleeve.

Instead of in each case processing only the signal of each individual resistance thermometer mounted in the feed stream or exit stream of one heating medium with the aid of a dedicated transducer assigned to it in each case to give a normalized output signal (overall, two different transducers are thus employed), which is then passed on to the process computer (a sensor for online measurement of a physical parameter to be measured consists generally of a sensor element which converts the measurement parameter to an electrical signal (for example the resistance thermometer) and a signal processor (a transducer) which first normally amplifies the electrical input signal and then converts it to a normalized electrical output signal which can be understood and processed by the process computer or by the process control system as a measured measurement parameter), it is possible with a single so-called temperature difference transducer not only to process each of the two signals arriving from the two resistance thermometers in an individualized manner to give the output signal corresponding to the particular temperature $T_H^{in}$ or $T_H^{out}$, and to pass them on to the process computer. Instead, the temperature difference transformer is capable additionally of forming the difference between the two output signals and of passing it on to the process computer as a signal corresponding to the temperature difference (e.g. $T_H^{in}-T_H^{out}$). This is advantageous in that any systematic error which occurs in the conversion of the individual signal is eliminated in the difference formation, which allows the temperature difference to be detected particularly accurately (accuracies in the detection of the temperature difference of $\leq \pm 0.05$ K are thus achievable). Preferably in accordance with the invention, the temperature difference transducer is a fieldbus transducer. This is a transducer which ensures an exclusively (entirely) digital signal transfer of the temperature difference to the process computer, which additionally makes possible transfer without loss of accuracy resulting from multiple conversion. In other transducers, the measurement signal (analog signal) perceived by the sensor is first digitalized in the sensor element (comprises a small "process computer") and then converted back to an analog normalized output signal, and supplied as such to the process computer. This multiple conversion may cause conversion errors to a certain degree.

Instead of resistance thermometers, the online temperature measurements required for the process according to the invention can in principle also be carried out with the aid of thermocouples. A thermocouple is a component composed of two different metals connected to one another at one end (the connection site). At the free ends of the two conductors connected to one another, an electrical voltage is generated in the event of a temperature difference along the conductors owing to the Seebeck effect. The connection site and the free ends must thus have different temperatures for this purpose. Employment of thermocouples for the process according to the invention therefore requires a stable comparative temperature in the environment of the free ends of the particular thermocouple, which is why their use is less preferred in accordance with the invention compared to use of the resistance thermometers.

As one means of obtaining the constant comparative temperature, the aforementioned comparative site can be accommodated, for example, in a bath of ice water (0° C.) or else in a thermostat (e.g. 50° C.). Alternatively, the connection of the measuring instrument can also be used as the comparative site, and the temperature there, which may be variable, can be detected with a thermistor or resistance thermometer in order to correct the thermal voltage measured numerically.

It is also possible to use integrated circuits for this correction, which not only serve as amplifiers for the voltage measured but also directly compensate the comparative site temperature, provided that they have the same temperature as the comparative site.

When the connection site is brought to the inlet site of a heating medium and the free ends are brought to the exit site of the heating medium, the thermal voltage which occurs is a direct measure of the difference $T^{in}-T^{out}$.

A further element to be taken into account in the heat balance to be established in accordance with the invention is the difference between the stream of perceptible heat fed to the secondary chamber through the feeding of the mass flow $\dot{m}_P$ of liquid phase P having an entrance temperature $T_P^{in}$ and the stream of perceptible heat conducted out of the secondary chamber by virtue of conducting out the mass flow $\dot{m}_S$ of (crystal) suspension S formed in the secondary chamber having an exit temperature $T_S^{out}$. This difference is, for example, given in a sufficiently good approximation for the process according to the invention by:

$$\dot{Q}_{P,in}=\dot{m}_P c_P^P \cdot (T_P^{in}-T_P^{out}) \qquad \text{(relationship 4)}.$$

In this relationship, $\dot{m}_P$ is necessarily identical to $\dot{m}_S$ owing to the conservation of mass.

$T_P^{in}$ and $T_S^{out}$ can be detected online using one of the sensors already detailed above, and $C_P^P$ is the mass-specific heat capacity based on heating at constant pressure (in simplified terms, frequently also just "mass-specific heat" in J/g·K) that the liquid phase P has.

It may, based on the entrance temperature $T_P^{in}$ and based on the entrance pressure of liquid phase P, be determined experimentally on entry into the secondary chamber, and then, for the purposes of the present invention, be assumed to be independent of pressure and temperature and be recorded as such in the process computer. $C_P^P$ can also be considered to be sufficiently robust with regard to limited variations in the composition of liquid phase P.

The precision of the determination of $\dot{Q}_{P,in}$ can, if required, for example, be increased by (as already described) monitoring the mass density of the suspension S conducted out of the secondary chamber of the heat exchanger online. Since this mass density correlates with the degree of crystallization Y of the suspension S, Y is obtainable online.

Instead of then inserting $C_P^P$ into relationship 4, it is also possible to calculate with $(C_P^P+C_P^S)/2$ in an improved approximation, where $C_P^S$ is the mass-specific heat capacity of the suspension S based on heating at constant pressure.

$C_P^S$ is calculated in a good approximation as $C_P^S \approx C_P^P \cdot (1-Y) + C_P^{Kr} \cdot Y$.

$C_P^{Kr}$ is the mass-specific heat capacity of the crystals based on heating at constant pressure.

$C_P^{Kr}$ is obtainable by calorimetric measurement for the boundary conditions of the process according to the invention and can otherwise be considered to be independent of temperature and pressure for the inventive purposes.

In general, $C_P^P$ and $C_P^S$ are substantially similar, such that a calculation solely with $C_P^P$ is sufficiently accurate. Quite generally, the degree of precision to be applied for the establishment of the heat balance required in accordance with the invention should be fixed with regard to the particular removal problem. For example, in the above approach, it should be taken into account that $\dot{Q}_{Kr,Y}$ is particularly large in the case of high Y (such that an approximation "$C_P^P \approx C_P^S$" does not become particularly disadvantageously noticeable in $\dot{Q}_{P,in}$) and the approximation "$C_P^P \approx C_P^S$" is particularly good in the case of small Y, since the crystal content and hence the contribution of $C_P^{Kr}$ weighted with it is low. With regard to large heat flows, the approach used must be more exact than in the case of small heat flows.

Finally, this leaves the consideration of diffuse heat flows which occur in the course of performance of a process according to the invention, which in total cause a total heat flow $\dot{Q}_D$ which, according to the boundary conditions set for performance of the process according to the invention, in balance terms, may be a heat flow flowing into the secondary chamber of the heat exchanger or a heat flow flowing out therefrom.

This heat flow is normally comparatively small compared to the other heat flows detailed. One reason for this is that the heat exchanger in which the crystallizative removal is carried out is normally insulated thermally from the environment by thermal insulation material applied externally to the heat exchanger (materials with low thermal conductivity coefficient $\lambda$ (W/m·K) such as wood, wood wool, fiber mats made of Chinese silvergrass, Poroton, mineral wool (e.g. glass wool), foam glass, polystyrene insulating materials such as the expanded polystyrenes Styropor®, Styrodur® and Neopor® (additionally comprises fine graphite particles), polyurethane insulating materials such as rigid polyurethane foam, carbon dioxide-PUR, c-iso-pentane-PUR, fumed silica (for example pressed plates thereof), evacuated PUR and evacuated silica). Entry of ambient air into the heat exchanger is normally substantially ruled out.

In addition, a water vapor barrier layer is generally applied to the heat insulation (for example an aluminum composite film according to EP-A 1 090 969 or DE 29 917 320 U1), which holds back the water vapor present in the ambient air and thus prevents condensation thereof on the heat exchanger which may have a low external temperature.

The thermal insulation is appropriately such that the dew-point temperature level is between water vapor barrier and heat exchanger surface. Frequently, the heat exchanger operated in accordance with the invention is additionally disposed in a closed housing and the air present between housing and thermally insulated heat exchanger equipped with the water vapor barrier is kept at a favorable temperature by thermostating. The material used for the accessible housing may in the simplest case be wood. Other materials such as plastic, sheet metal, brickwork or concrete are also possible. Frequently, the temperature difference between the air temperature in the housing and $T_S^{out}$ is less than 25 K.

Any heat flows introduced into the fluid contents of the secondary chamber by the optionally moving wiper and/or stirrer apparatus in the secondary chamber are normally likewise relatively weak (small) heat flows.

In an approximation sufficiently accurate for the process according to the invention, $\dot{Q}_D$ can therefore be determined by a "water run".

In other words, the heat exchanger is filled, for example, with a liquid (e.g. water; in general, though, any other substance which is in the liquid state of matter under the appropriate boundary conditions can also be used) whose temperature is $(T_P^{in}+T_S^{out})/2$ where $T_P^{in}$ and $T_S^{out}$ are the values contemplated for the regular operation of the crystallizer. The moving parts, for example the wiper apparatus and/or stirrer apparatus, in the secondary chamber are then put into operation and the temperature of the water present in the secondary chamber is monitored as a function of time.

According to the relationship $\dot{Q}_D = (C_P^{Fl} \cdot \Delta T)/\Delta t$, where $\Delta T$ is the temperature difference of liquid present in the secondary chamber of the heat exchanger which occurs within the time interval $\Delta t$ and $C_P^{Fl}$ here is the corresponding absolute heat capacity based on constant pressure (absolute heat, enthalpy) of the liquid-filled heat exchanger at the temperature $(T_P^{in}+T_S^{out})/2$. $C_P^{Fl}$ is determined beforehand in a separate "water run", in which a particular (a defined) amount of heat is fed to the liquid-filled heat exchanger (for example with an immersion boiler switched on for a defined period and immersed into the liquid) and the associated temperature change is observed. In an even simpler manner, $\dot{Q}_D$ is obtainable in a water run by conducting, for example, a steady-state water mass flow $\dot{m}_w$ whose temperature $T_W^{in}$ on entry into the secondary chamber corresponds to the temperature $T_P^{in}$ the inventive operation of the heat exchanger through the secondary chamber of the heat exchanger operated without trace heating as the liquid phase P. At the same time, coolant is conducted through the at least one primary chamber of the heat exchanger such that the water flow leaves the secondary chamber of the heat exchanger in a steady state with a temperature $T_W^{out}$ that corresponds to the temperature $T_S^{out}$ in the inventive operation of the heat exchanger.

From the relationship $$\dot{m}_W \cdot C_P^W \cdot (T_W^{out} - T_W^{in}) - \dot{m}_K \cdot Q_P^K \cdot (T_K^{out} - T_H^{in}) = \dot{Q}_D,$$

the diffuse total heat flow is obtainable in a simple manner. $C_P^W$ here is the mass-specific heat capacity based on constant pressure of the water used for the water run or the liquid otherwise used for this water run (at the temperature $T = (T_W^{out} + T_W^{in})/2$). The $\dot{Q}_D$ thus determined is recorded as a constant in the process computer.

The overall heat balance is thus calculated as follows:

$$\dot{Q}_{Kr,y} = \dot{Q}_{K,out} - \dot{Q}_{H,in} - \dot{Q}_{P,in} - \dot{Q}_D \qquad \text{(relationship 5)}$$

(normally, $\dot{Q}_D$ will be entered into relationship 5 with a positive sign; in principle, it may, though, also be entered into relationship 5 with a negative sign; the sign is decided by the result of the water run described; the case of a positive sign corresponds to a heat flow $\dot{Q}_D$ flowing into the secondary chamber).

Using the normalized output signals released continuously to the process computer by the sensors used, the process computer can continuously calculate the value of both sides in relationship 5. When they are equal, there is no need to initiate closed-loop control measures.

When, however, the values calculated for both sides of relationship 5 are different from one another, there is a need for closed-loop control in order to maintain the degree of crystallization Y. The process computer then controls parameters selected as a result of the deviation of the results determined for the two sides, the change in which influences variable heat flows on the right-hand side of relationship 5 ($\dot{Q}_D$ is a constant) such that the value on the right-hand side of relationship 5 is moved gradually back toward the value of the guide parameter $\dot{Q}_{Kr,Y}$. During the movement, there is constant adjustment of the values calculated currently for both sides of relationship 5 and, resulting from this, continuous adjustment of the influence on the control parameter. Preference is given in accordance with the invention to addressing of control parameters which influence $\dot{Q}_{K,out}$. Particular preference is given to addressing of control parameters which influence $T_K^{in}$.

When relationships 1 to 4 are inserted into relationship 5, the overall heat balance is calculated, for example, as follows:

$$\underline{\dot{m}_P} \cdot Y \cdot C_{Kr} = \underline{\dot{m}_K} \cdot C_P^K \cdot \left( \underline{T_K^{out}} - \underline{T_K^{in}} \right) - \qquad \text{(relationship 6)}$$

$$\underline{\dot{m}_H} \cdot C_P^H \left( \underline{T_H^{in}} - \underline{T_H^{out}} \right) - \underline{\dot{m}_P} \cdot C_P^P \left( \underline{T_P^{in}} - \underline{T_P^{out}} \right) - \dot{Q}_D.$$

In this relationship, the terms underlined in bold are those which can be monitored online experimentally by means of the sensor elements indicated and can be passed on to the process computer without time delay via accompanying transducers, while the terms not underlined in bold are recorded in the process computer (are part of the software).

It should be emphasized at this point that, by virtue of trial experiments before the actual inventive crystallizative removal, to increase the precision of the process according to the invention, an adjustment of the terms recorded in the process computer, i.e. terms not monitored online, to the results achieved in the trial experiments for Y is normally also undertaken (fine tuning). In other words, different steady operating states of the crystallizative removal are defined (set), which generally also have different degrees of crystallization Y, and the quality of the balance which arises in arithmetic terms for these states between the two sides of relationship 6 is used to undertake adjustments to the recorded values which improve the quality of the balance.

At this point, it should also be emphasized that, in the case that the secondary chamber of the heat exchanger is in contact with a plurality of mutually spatially separated primary chambers (in a wiped plate heat exchanger, for example, the interior of each individual cooling disk forms such a primary chamber), and each individual primary chamber is operated with a cooling medium which is, for example, a different substance than the cooling media conducted into the other primary chambers and is conducted independently, relationship 6 is maintained, except that, on the right-hand side, for example, is a sum of expressions "$\dot{m}_K \cdot C_P^K (T_K^{out} - T_K^{in})$", where each summand represents one primary chamber. Otherwise, it is possible to proceed in an entirely equivalent manner to that described below using the example of the use of only one coolant substance.

Preferably in accordance with the invention, in the case that the secondary chamber is in contact with a plurality of primary chambers, all primary chambers are flowed through by one and the same coolant substance (this coolant substance may, if appropriate, be guided through some of the primary chambers independently (separately) from the flow through another or a plurality of others).

Immediately beyond (or immediately before) the coolant outlet from the particular primary chamber, in this case, the different coolant streams which leave in each case, appropriately in application terms, can be combined to a single overall coolant stream whose mixing temperature then forms the relevant $T_K^{out}$ which is monitored online in accordance with the invention for relationship 6. This overall coolant stream is then brought back to the temperature $T_K^{in}$ relevant for relationship 6 and then, as required, distributed between the different primary chambers or some of them.

It is possible to proceed in a corresponding manner to that in the case of a plurality of primary chambers flowed through by coolant when more than one trace heating system by indirect heat exchange is employed in the process according to the invention. Otherwise, in the process computer (process computers (frequently also a process control system (PCS), i.e. a network of computers) are computers which are characterized by the following parameters: input signals, exclusively from sensors; output signals are transmitted exclusively via actuators; the data is processed in real time; only the programming is effected by human input; actuators are the transducer-based counterpart to sensors and form the control element in a closed-loop control structure; they usually convert closed-loop control signals coming from the process computer to mechanical work, i.e. movements, for example a valve which opens or closes; in other words, actuators, viewed in technical terms, are the connection of an energy transducer to a power control element; the power control element connects the input energy (generally electrical energy) to the control signal; it gives rise to a modulated energy which is transformed by the transducer to the energy type of the control parameter (usually mechanical energy)), the left-hand side of relationship 6 (or 5) is compared continuously with the right-hand side of relationship 6 (or 5).

When the two sides are of equal magnitude, there is no need for closed-loop control to maintain the degree of crystallization Y. When the heat flows on the two sides are different from one another, there is a closed-loop control deviation from the target value "0" for the difference between the two sides. When, for example, the left-hand side is larger than the right-hand side, preference will be given to a closed-loop control intervention such that the value of the expression $\dot{m}_K \cdot C_P^K (T_K^{out} - T_K^{in})$ increases (otherwise, Y would undesirably fall as a consequence of the closed-loop control deviation). For this purpose, normally control parameters which are addressed by the process computer and, by virtue of their change, influence $\dot{m}_K$ and/or $T_K^{in}$ will be utilized. A corresponding rise in $\dot{m}_K$ and/or a lowering of $T_K^{in}$ can be used to counteract the closed-loop control deviation. For reasons relating to flow, the closed-loop control margins are typically comparatively restricted with regard to an adjustment of $\dot{m}_K$. Against this background, preference is therefore usually given to counteracting a closed-loop control difference only with a change in $T_K^{in}$.

Advantageously, a closed-loop control deviation will therefore be detected directly by a balance with respect to $T_K^{in}$.

For this purpose, in the process computer, relationship 6 is, appropriately in application terms, resolved as follows:

$$T_K^{in} = T_K^{out} - \frac{\dot{m}_H \cdot C_P^H (T_H^{in} - T_H^{out}) + \dot{m}_P \cdot C_P^P (T_P^{in} - T_S^{out}) + Q_D + \dot{m}_P \cdot Y \cdot C_{Kr}}{\dot{m}_K \cdot C_P^K}. \quad \text{(relationship 7)}$$

The right-hand side is determined continuously in the process computer and compared with $T_K^{in}$ which is amenable to an online determination. When, for example, the right-hand side is greater than the left-hand side, the closed-loop control deviation will be counteracted by increasing $T_K^{in}$.

To this end, the procedure may, for example, be as follows. In principle, only a substream from the coolant stream leaving the heat exchanger will be fed to a thermostated reservoir of coolant to leave a residual stream and is cooled on the way to the reservoir by indirect heat exchange to the comparatively low temperature existing in the thermostated reservoir (it may be up to 10 K or more below the steady-state $T_K^{in}$). The substream conducted to the reservoir is simultaneously balanced out by withdrawing a correspondingly large substream from the reservoir, mixing it with the residual stream and then feeding the resulting mixture back to the heat exchanger. The magnitude of the two substreams is adjusted, for example, by means of corresponding vanes or valves addressed by the process computer with the aid of actuators as the control parameter such that the mixture has the value of $T_K^{in}$ required in each case. If, as a consequence of a closed-loop control deviation, for example, $T_K^{in}$ should be increased, the substream is reduced in a controlled manner by the process computer.

If, as a consequence of a closed-loop control deviation, $T_K^{in}$ should be reduced, the substream is increased in a controlled manner by the process computer. As a result of the increase or reduction in $T_K^{in}$, the process computer corrects the value on the two sides of relationship 7 until equality is attained again. Appropriately in application terms, the recycling of the substream of the coolant stream leaving the heat exchanger to be recycled to the thermostated coolant reservoir, with simultaneous withdrawal of a corresponding substream from the reservoir, can also be configured as follows.

A pumped circuit of the coolant functions as the coolant reservoir, which, for example, on the brine side, is conducted through the indirect evaporator of an ammonia compression refrigeration system. An amount of ammonia corresponding to the feed temperature of the pumped coolant flow to the indirect evaporator is liquefied beforehand and evaporated by the coolant stream flowing through the evaporator, with cooling thereof, to the intended thermostating temperature (the evaporation temperature of the ammonia is adjusted by means of the suction pressure of the compressor (this procedure is also referred to as suction pressure regulation)).

The recycling of the substream of the coolant stream leaving the heat exchanger to be recycled to the thermostated reservoir is now undertaken by means of a feed valve which regulates the substream flow rate into the brine-side feed stream to the indirect evaporator of the ammonia compression refrigeration system, and the corresponding simultaneous substream withdrawal from the reservoir is effected by means of a corresponding withdrawal valve which regulates the substream flow rate from the brine-side exit stream of the indirect evaporator of the ammonia compression refrigeration system. The valve openings are addressed again by the process computer according to the substream flow rate required to establish the particular $T_K^{in}$.

Alternatively, it is also possible for only the coolant stream conducted from the coolant reservoir to the heat exchanger to be regulated by means of a valve. The coolant stream which flows from the heat exchanger back to the coolant reservoir then results automatically. In this case, the process computer addresses only this one valve opening.

This procedure for adjusting $T_K^{in}$ shall be referred to in this document as the ammonia compression process.

Corresponding circulation methods enable, if required, a change in $T_H^{in}$. In this case, a thermostated heating medium reservoir at elevated temperature is included.

It is even more beneficial in accordance with the invention to connect a closed-loop control deviation directly to the temperature difference $T_K^{in} - T_K^{out}$.

For this purpose, in the process computer, relationship 6 is advantageously resolved as follows:

$$(T_K^{out} - T_K^{in}) = \frac{\dot{m}_H \cdot C_P^H (T_H^{in} - T_H^{out}) + \dot{m}_P \cdot C_P^P (T_P^{in} - T_S^{out}) + Q_D + \dot{m}_P \cdot Y \cdot C_{Kr}}{\dot{m}_K \cdot C_P^K}.$$

relationship 8

The reason for the advantageousness is that, as already stated in this document, the temperature difference $T_K^{out} - T_K^{in}$ when corresponding resistance thermometers are used in the inlet to and in the outlet from the particular primary chamber of the heat exchanger and with use of a fieldbus temperature difference transducer, can be conducted as the input signal to the process computer free of systematic transducing errors and directly in digitalized form. The comparison with the right-hand side of relationship 8 is then effected in the process computer and, when a closed-loop control deviation is found, the appropriate actuator for the control parameter to be influenced can be addressed directly using it either in digitalized from (requires a further fieldbus for the actuator) or in analog form (for example with normal signal from 4 to 20 mA). The use of a fieldbus (cf. DIN 19245 and IEC-61158-2) thus enables a constant digital information exchange between sensor and actuator (for example with a PROFIBUS-PA or a Foundation Fieldbus), which makes possible a particularly high level of closed-loop control precision. When the left-hand side is, for example, smaller than the right-hand side, there is a need for closed-loop control. In order to counteract this closed-loop control deviation, preference is given to increasing $T_K^{in}$, as already described above, to an appropriate degree as required until the values on the two sides of the relationship 8 correspond again.

One impressive feature of the inventive closed-loop control system is that it reacts comparatively rapidly to perturbations relevant to the degree of crystallization Y, and another is that it behaves comparatively robustly with respect to perturbations which are generally irrelevant for the degree of crystallization Y. It additionally has a high stability and a very good static accuracy and low tendency to overshoot.

In principle, all kinds of indirect heat exchangers are useful for the performance of the process according to the invention (by definition, they have the primary chamber/secondary chamber structure required in accordance with the invention) (cf., for example, Kristallisation, Grundlage und Technik [Crystallization, Fundamentals and Technology], Günther Metz, Springer-Verlag, Berlin 1969, p. 214 ff. and Ullmanns Encyclopädie der technischen Chemie, Verfahrenstechnik I [Process Technology I], Verlag Chemie Weinheim, 4th edition, 1972, page 672-682, and the prior art mentioned in these standard works).

The problem of the development of crust formation on the side of the dividing wall (heat exchange wall) between primary chamber and secondary chamber which faces the secondary chamber has already been addressed. As already mentioned, it can be counteracted, for example, by continuous scratching of the relevant heat-transferring area with the aid of suitable wiper apparatus. Such heat exchangers (coolers) are also referred to as scraped-surface coolers. Alternatively, it is also possible to use moving primary chamber elements (for example removable cooling disks) for this purpose, and to replace them from time to time.

The conveying motion of the fluid phase present in the secondary chamber through said chamber is in many cases already sufficient to cause suspension of the crystals removed in the secondary chamber. In general, however, the secondary chamber additionally has one or more mixing devices. In the simplest case, this may be sparging with an auxiliary gas (e.g. air), one or more stirrers, the wiping apparatus and/or pumped circulation. The conveying of the mass flow fed to the secondary chamber through said chamber is normally accomplished by forcing liquid phase P into the secondary chamber with the aid of pumps. The removal of (crystal) suspension S from the secondary chamber is effected typically under overflow control (but it can also be effected under level control through an immersed tube). For this purpose, advantageously in application terms, a height-adjustable overflow weir is used.

As an illustrative selection, the following can be used for the process according to the invention:

rotary tube crystallizers (the secondary chamber is the tube interior; the tube shell is a jacket within which the coolant is conducted in occurrent or in countercurrent to the mass flow inside the tube; the tube interior is preferably slightly tilted from the horizontal; crystal crusts forming on the tube interior wall can continuously be knocked off (for example with chains) and/or scratched off (e.g. with radial wipers); the liquid phase P is fed continuously into one end of the tube; the suspension S is conducted out continuously at the other end of the tube);

a vessel with hung cooling elements (cooling elements (e.g. cooling disks) are hung in an unstirred vessel; the liquid phase P is, for example, conducted into the vessel bottom left, and the suspension S is conducted out of the vessel under overflow control top right; cooling elements having encrustations are replaced by fresh cooling elements);

stirred vessels (these are, for example, vessels which are surrounded by a cooling jacket and/or equipped with cooling elements (cooling coils, cooling disks); in addition, they have a stirrer which mixes the contents of the interior not occupied by the cooling elements continuously by stirring; the liquid phase P is fed in by pumps and the suspension S is conducted out by overflow);

votator (jacket-cooled tube at rest, whose wall is scraped by flat scratching blades pressed on with springs; the liquid phase P is pumped in at one end, the suspension S flows out at the other end);

pan crystallizer (trough-like vessel with horizontal shaft on which are mounted, at regular intervals, hollow pans (hollow disks) which are flowed through by the cooling medium generally in countercurrent to the crystallizing liquid phase P and which have sector-shaped cutouts for the passage of liquid phase P or crystal suspension; gentle stirring of the crystal suspension through the pans and the coolant lines connecting them; the liquid phase P is conducted into the pan crystallizer on one side by pumps and conducted out of the pan crystallizer under overflow control on the opposite side);

forced-circulation crystallizer from Swenson or Messo Chemietechnik.

Crystallizers particularly suitable for the process according to the invention (especially in the case of acrylic acid, methacrylic acid, p-xylene or N-vinylpyrrolidone as target product X) are cooling disk crystallizers (cooling disks present in the secondary chamber comprise the primary chambers), for example those disclosed in Research Disclosure Database Number 496005 (published in August 2005) and in Research Disclosure Database Number 479008 (published in March 2004).

The fluid coolants (or assistants) used may be either gases or liquids.

Preference is given in accordance with the invention to using liquid coolants (or heating media). Useful such liquid coolants (or heating media) include, for example, heat carrier oils, water, solutions of salts in water, mono- or polyhydric organic alcohols such as methanol, ethanol, propanol, glycol and/or glycerol, but also mixtures of one or more of the aforementioned coolants, for example water/methanol mixtures or water/glycol mixtures (for example with from 10 to 60% by weight of glycol).

The temperature $T_K^{in}$ in an inventive cooling crystallization is typically set from 0 to 20 K, often from 1 to 15 K and usually from 2 to 10 K below $T_S^{out}$. The temperature $T_H^{in}$ is appropriately selected within a range above $T_S^{out}$, for example in the range from 0 to 20 K, often from 0.5 to 10 K and usually from 1 to 5 K higher.

The suspension crystals which form in the course of performance of the process according to the invention typically have a longitudinal dimension (longest direct straight line connecting two points on the crystal surface) in the range from 1 to 10 000 µm, often from 10 to 1000 µm, frequently from 100 to 800 µm and in many cases from 300 to 600 µm.

Otherwise, the crystallizative removal can be performed like the suspension crystallizations performed in the prior art.

The (crystal) suspension S conducted out of an inventive removal is normally not fed directly to its separation into crystals and residual phase R (mother liquor). Instead, it is buffered intermediately in a tank which is, for example, stirred and/or pumped in circulation and withdrawn continuously therefrom and fed, for example, to a wash column removal. When a plurality of (for example two or three) crystallizers (heat exchangers), for example of identical design, are operated in parallel in the inventive manner (each of the crystallizers operated in parallel preferably has a dedicated inventive control (setting) (independent of the other crystallizers) of the degree of crystallization Y achieved therein; the particular coolant circuits and, if appropriate, heating medium circuits are supplied, advantageously in application terms, from a thermostated coolant reservoir or heating medium reservoir common to all crystallizers), all suspensions S conducted in each case out of the different crystallizers are, appropriately in application terms, first fed to a common buffer tank and mixed therein by stirring. From this buffer tank, the separating apparatus for the mother liquor/crystal separation is then charged (for example hydraulic wash columns whose number advantageously corresponds to that of the crystallizers operated in parallel (in principle, it may, though, also be greater or smaller) and which are likewise operated in parallel and are typically likewise of the same design). The molten pure product withdrawn, for example, from the melt circuit of the particular wash column is fed to a combined storage tank in which the arriving pure product streams are mixed with one another.

From the storage tank, the pure target product X (polymerization-inhibited if appropriate) can then be fed to the particular consumer. Appropriately in application terms, on the way from the buffer tank to the mother liquor/crystal separation, an additional test of the degree of crystallization Y of the crystal suspension can be undertaken as a precautionary measure with the aid of a coriolis mass flow meter by means of a determination of its mass density.

The present invention thus comprises especially the following embodiments:

1. A process for continuously removing a target product X in the form of fine crystals of the target product X from a liquid phase P comprising the target product X and constituents other than the target product X with the aid of a heat exchanger having a secondary chamber and at least one primary chamber, in which the secondary chamber and the at least one primary chamber are each spatially separated from one another by at least one material dividing wall which serves as an area for transferring heat out of the secondary chamber into the at least one primary chamber, in which liquid phase P is conducted continuously into the secondary chamber of the heat exchanger, while the at least one primary chamber is simultaneously flowed through by at least one fluid cooling medium such that fine crystals of the target product X are formed from the liquid phase P in the secondary chamber to leave a liquid residual phase R and are suspended in the remaining liquid residual phase R which, compared to the liquid phase P, comprises the constituents other than the target product X in enriched form and whose content of target product X is at least 70% by weight to obtain a suspension S of fine crystals of the target product X in the liquid residual phase R which has a degree of crystallization Y, and suspension S is conducted continuously out of the secondary chamber of the heat exchanger, wherein the desired degree of crystallization Y of the suspension S conducted out of the secondary chamber of the heat exchanger is established by employing the difference, determined at the particular operating time with the aid of a process computer, between the flow of heat of crystallization $\dot{Q}_{Kr,Y}$ which develops in theoretical terms in the secondary chamber according to the degree of crystallization Y, and the difference formed between the heat flow $\dot{Q}_{out}$ otherwise conducted overall out of the secondary chamber of the heat exchanger and the heat flow $\dot{Q}_{in}$ in otherwise conducted overall into the secondary chamber of the heat exchanger.

2. The process according to embodiment 1, wherein the content in the liquid residual phase R of target product X is ≧80% by weight.

3. The process according to embodiment 1, wherein the content in the liquid residual phase R of target product X is ≧90% by weight.

4. The process according to any of embodiments 1 to 3, wherein the target product X is acrylic acid, methacrylic acid, p-xylene or N-vinylpyrrolidone.

5. The process according to any of embodiments 1 to 4, wherein the liquid phase P comprises at least two constituents other than the target product X.

6. The process according to any of embodiments 1 to 5, wherein the liquid phase P is crude acrylic acid which has the following contents:
≧85% by weight of acrylic acid,
≧100 ppm by weight to ≦10% by weight of acetic acid,
≧10 ppm by weight to ≦5% by weight of propionic acid,
up to 5% by weight of low molecular weight aldehydes,
up to 3% by weight of polymerization inhibitors,
0 to 5% by weight of diacrylic acid,
up to 10% by weight of water.

7. The process according to any of embodiments 1 to 6, which comprises, in addition to the process step according to embodiment 1, the following process steps:
b) separating the suspension S conducted out of the secondary chamber of the heat exchanger into crystals of the target product X and liquid residual phase R,
c) at least partly melting the crystals of the target product X removed and
d) at least partly recycling the molten crystals of the target product X to step b) and/or to the process step for continuous removal of target product X according to embodiment.

8. The process according to any of embodiments 1 to 6, which is followed by a process for continuously removing fine crystals of the target product X present in the suspension S, in which
the suspension S is fed to a wash column which has a wash column wall which surrounds a process chamber,
liquid residual phase R is released from the process chamber while retaining the crystals present in the suspension S to form a crystal bed in the process chamber from the suspension S conducted into the process chamber by means of filter equipment,
the crystal bed is conveyed within the process chamber,
at least one force other than gravity acts in the process chamber in the conveying direction of the crystal bed and conveys the crystal bed within the process chamber,
pure melt which consists of molten crystals which have been removed beforehand by this wash column process is conducted within the process chamber in countercurrent to the crystal bed such that a wash front which divides the crystal bed into a mother liquor zone and into a pure melt zone forms in the crystal bed, and
crystals in solid and/or molten form which have been washed in the wash column are discharged continuously at the opposite end of the wash column to the feed of the suspension S.

9. The process according to embodiment 8, wherein the target product is acrylic acid and the process is followed by a further process in which molten and removed acrylic acid crystals are subjected to a polymerization with themselves or with other at least monoethylenically unsaturated compounds.

10. The process according to any of embodiments 1 to 9, wherein the liquid phase P is conducted into the secondary chamber of the heat exchanger with the mass flow intensity $\dot{m}_P$ and the process comprises a determination of the mass flow intensity $\dot{m}_P$ and/or of the intensity of the volume flow corresponding to $\dot{m}_P$.

11. The process according to embodiment 10, wherein the mass flow intensity $\dot{m}_P$ is determined with the aid of a coriolis mass flow meter, or of a vortex flow meter, or of a magnetic-inductive flow meter, or of a variable area flow meter.

12. The process according to any of embodiments 1 to 10, wherein the liquid phase P is conducted into the secondary chamber with a temperature $T_P^{in}$ and the suspension S is conducted out of the secondary chamber with a temperature $T_S^{out}$, and the process comprises a determination of $T_P^{in}$, of $T_S^{out}$ and of $T_P^{in}-T_S^{out}$.

13. The process according to embodiment 12, wherein the determination of $T_P^{in}$ and of $T_S^{out}$ is carried out in each case with a resistance thermometer.

14. The process according to embodiment 13, wherein the resistance thermometer is a platinum resistance thermometer.

15. The process according to any of embodiments 1 to 14, wherein the fluid cooling medium flowing through the at least one primary chamber is conducted into the at least one primary chamber with a temperature $T_K^{in}$ and is conducted out of the at least one primary chamber with the temperature $T_K^{out}$, and the process comprises a determination of $T_K^{in}$, $T_K^{out}$ and of $T_K^{out}-T_K^{in}$.

16. The process according to embodiment 15, wherein the determination of $T_K^{in}$ and $T_K^{out}$ is carried out in each case with a resistance thermometer.

17. The process according to embodiment 16, wherein the resistance thermometer is a platinum resistance thermometer.

18. The process according to embodiment 15, wherein the determination of the difference of $T_K^{out}-T_K^{in}$ is carried out with two resistance thermometers and only one temperature difference transducer.

19. The process according to embodiment 18, wherein the temperature difference transducer is a fieldbus transducer.

20. The process according to any of embodiments 1 to 19, wherein the fluid cooling medium flowing through the at least one primary chamber is conducted into the at least one primary chamber with the mass flow intensity $\dot{m}_K$ and the process comprises a determination of the mass flow intensity $\dot{m}_K$ and/or the intensity of the volume flow accompanying $\dot{m}_K$.

21. The process according to embodiment 20, wherein the mass flow intensity $\dot{m}_K$ is determined with the aid of a coriolis mass flow meter, or of a vortex flow meter, or of a magnetic-inductive flow meter, or of a variable area flow meter.

22. The process according to any of embodiments 1 to 21, wherein the cooling medium which flows through the at least one primary chamber is conducted into the at least one primary chamber with the temperature $T_K^{in}$ and, in the case that the difference between $\dot{Q}_{Kr,Y}$ and the difference $\dot{Q}_{out}-\dot{Q}_{in}$ is not vanishing, $T_K^{in}$ is changed.

23. The process according to any of embodiments 1 to 22, wherein the target product X is acrylic acid which has been obtained by a heterogeneously catalyzed partial gas phase oxidation.

24. The process according to any of embodiments 1 to 23, wherein the target product X is acrylic acid, and the liquid phase P is derived from a fractional condensation and/or absorption of the product gas mixture of a heterogeneously catalyzed partial gas phase oxidation to prepare acrylic acid.

25. The process according to any of embodiments 1 to 24, wherein the heat exchanger is a cooling disk crystallizer.

26. The process according to any of embodiments 1 to 25, wherein the coolant used is a mixture of water and methanol or a mixture of water and glycol.

27. The process according to any of embodiments 1 to 26, which is followed by a determination of the mass density of the suspension S with the aid of a coriolis mass flow meter.
28. The process according to any of embodiments 1 to 27, wherein Y is from 0.10 to 0.50.
29. The process according to any of embodiments 1 to 27, wherein Y is from 0.20 to 0.40 or from 0.25 to 0.35, or 0.30.
30. A process for preparing a target product X, which comprises a process according to any of embodiments 1 to 8 or according to any of embodiments 10 to 29.

The principle of heat balancing which underlies the inventive adjustment of the degree of crystallization Y in a continuous crystallizative removal can also be applied in the case of a batchwise or semicontinuous crystallizative removal. Instead of with reference to heat flows fed in and removed, the heat balancing is then effected, however, on the basis of the amounts of heat fed in and removed. For their calculation, start and end temperatures replace the entrance and exit temperatures, and masses summed over time (integrals) replace mass flows.

EXAMPLE

Two identical stirred and wiped cooling disk crystallizers of the design described in Research Disclosure Database Number 496005 (published in August 2005) were operated in parallel (alternatively, it is also possible for three of these crystallizers to be operated in parallel in each case with two of the wash columns or with three of the wash columns). These were each a trough in which 24 wiped circular cooling plates at an equidistant interval of 30±1 cm were arranged hung in succession. The plate diameter was 3.3 m. The plate thickness was 5.2 cm.

The coolant used for each of the two crystallizers was a mixture of 70% by weight of water and 30% by weight of glycol. The coolant was conducted through the crystallizer in countercurrent to the liquid phase P fed to the crystallizer in the particular crystallizer, and passed on from cooling disk to the next cooling disk but one. In other words, the coolant in each of the two crystallizers was conducted divided in the form of two equal and parallel streams through the cooling plates of the particular crystallizer. Half of the stream led through the numerically even cooling plates; the other half stream led through the numerically odd cooling plates (numbering of the cooling disks in flow direction of the coolant beginning with 1). The cooling areas were manufactured from stainless steel (DIN material 1.4541). The wall thickness of the stainless steel cooling areas was 4 mm. The rotation speed of the wipers was 6 revolutions per minute. The shaft conducted through the center of the cooling disks, which drives the wipers, was sealed with water-flushed stuffing box packings (packing threads made of Teflon; flush rate=a few liters per hour up to a few 10 s of l/h per seal). On the circumference of each cooling disk, where it is not possible to wipe, a hollow profile was mounted (a tube welded on; (material: stainless steel (DIN material 1.4541), wall thickness 3.6 mm)). For the purpose of trace heating the individual cooling disks of a crystallizer, a liquid heating medium flowed in parallel in to the hollow profile thereof, which was likewise composed of 70% by weight of water and 30% by weight of glycol.

The wipers were segmented in the radial direction (4 segments).

The specific pressing force of the wipers in the installed state at right angles to the cooling surface was about 4 N per cm of active wiping edge length. The wiper material used was Multilene® PE 1000. In addition to the wipers, the shaft drove paddles (between two cooling disks and before the first and last cooling disk, in each case in symmetrical arrangement), which brought about improved mixing. In the back part of the particular crystallizer in conveying direction of the crystal suspension (beyond the last cooling disk), the (crystal) suspension S formed in the individual crystallizer in each case flowed over an overflow weir into a common buffer tank stirred with a helical stirrer (made of stainless steel of DIN materials No. 1.4541 or 1.4571; with the aid of slight trace heating thereof, it is possible if required to bring about the degradation of an existing oversaturation of the suspension S), from which two identical hydraulic melt wash columns were charged in parallel with suspension S withdrawn from the buffer tank in two roughly equal partial mass flows (separation of the mass flow of suspension S withdrawn from the buffer tank between the two wash columns was followed in each case, before entry into the particular wash column, by flow through a coriolis mass flow meter for the purpose of determining the degree of crystallization Y via the mass density of the particular partial mass flow) for the purpose of separating it into residual phase R and crystals. The separation in the melt wash columns was effected as described in documents EP-A 1 272 453, WO 2006/111565, EP-A 1 448 283, WO 03/041833, EP-A 1 305 097, DE-A 101 56 016, DE-A 10 2005 018702, DE-A 102 23 058 and German application 10 2007 004 960.0. The internal diameter of the individual wash column was 1.4 m. The wash columns were charged with crystal suspension S in each case by means of a centrifugal pump (Kanalrad type), and the flow was controlled by means of speed regulation of the pumps.

The mass flow of (crystal) suspension S fed to the particular wash column corresponded essentially to the mass flow of suspension S overflowing from an individual crystallizer into the buffer tank. The steady-state contents in the buffer tank of crystal suspension S were 16 $m^3$.

Each of the two crystallizers had a roof (stainless steel (DIN material 1.4541)) and was sealed against ingress of ambient air. Both the wash columns, which were likewise manufactured from stainless steel (DIN material 1.4541, wall thickness 10 mm) and the crystallizers and the buffer tank were provided with a steam barrier (cf., for example, DE-A 10 2007 032 633) and thermally insulated by means of Alu-Butyl foil from WeGo Systembaustoffe, VTI branch in 67014 Ludwigshafen/Rhein adhesive-bonded to their stainless steel shell applied Styropor.

The wash columns, the buffer tank and the crystallizers were accommodated in a common housing. The air temperature in the overall housing was between 25° C. and 28° C. The mass transfer from the crystallizers into the buffer tank and from there into the wash column was effected likewise sealed from the ambient air, and also with heat insulation and water vapor sealing.

The degree of crystallization Y was established independently in the inventive manner for each of the two crystallizers operated in parallel. The value for Y defined for the two crystallizers for this purpose was a uniform 0.28. This degree of crystallization was set for each of the two crystallizers on the basis of relationship 8, irrespective of that of the other crystallizer. A closed-loop control deviation was counteracted in both cases by a sole increase or decrease in the particular $T_K^{in}$. The particular $T_K^{in}$ was adjusted for each of the two crystallizers by the ammonia compression process, except that a common coolant reservoir was used.

The heating medium feed stream fed to the particular crystallizer was, on entry into the particular crystallizer, divided into a number of parallel substreams corresponding to the number of cooling disks in the crystallizer, which, after in each case passing through the hollow profile welded on the particular cooling disk, before leaving the crystallizer, were combined again to form one heating medium removal stream. The entrance temperature $T_H^{in}$ of the particular heating medium feed stream was kept uniformly at a constant value of 12° C. for the two crystallizers over the overall operating time. To adjust $T_H^{in}$, all heating medium removal streams were combined to one overall heating medium removal stream.

An appropriate substream of this overall heating medium removal stream (regulated by means of a control valve controlled by the process computer) was fed to a heating medium reservoir whose reservoir temperature was kept at a value of from 20 to 50° C., and a corresponding substream was simultaneously withdrawn from the reservoir and mixed with the remaining residual stream to give the new overall heating medium feed stream having the required temperature $T_H^{in}$. This was again divided into the two heating medium feed streams and these were fed again to the particular crystallizer. The intensity of the heating medium feed stream fed to the particular crystallizer was likewise kept constant over the entire operating time.

For application of an independent inventive heat balance regulation of its degree of crystallization Y, each crystallizer and the accompanying dedicated coolant circuit, as well as a dedicated process calculation, was equipped with the following sensors and actuators:

a) for $T_K^{in}$, $T_K^{out}$ and $T_K^{out} - T_K^{in}$:
   a temperature difference transducer of the 3144P type with digital data transfer to the PCS via a "Foundation Fieldbus" type
   two MEW Pt100 resistance thermometers in a protective tube; (all aforementioned elements from Rosemount/Emerson Process Management, 8200 Market Boulevard Chanhassen, Minn. 55317, USA);

b) for $\dot{m}_K$:
   an IFM 4042K magnetic inductive flow meter from Krohne, D-47058 Duisburg, data transfer to the PCS with an (analog) standard signal 4-20 mA (the 4 mA correspond to the start of the measurement range, the 20 mA to the end of the measurement range);
   the mass density of the coolant was recorded in the measuring instrument at the value of 1055 g/dm³ as a constant;

c) for $T_H^{in}$ and $T_H^{out}$:
   two MEW Pt 100 resistance thermometers in a protective tube;
   for each resistance thermometer, one type 248 temperature transducer, data transfer to the PCS with standard signal 4-20 mA;
   (all aforementioned elements from Rosemount/Emerson);

d) for $\dot{m}_H$:
   H250 variable area flow meter from Krohne, data transfer to the PCS with standard signal 4-20 mA; the mass density of the coolant was recorded in the measuring instrument at the value of 1055 g/dm³ as a constant;

e) for $T_P^{in}$ and $T_S^{out}$:
   two MEW Pt 100 resistance thermometers in a protective tube;
   for each resistance thermometer, a type 248 temperature transducer, data transfer to the PCS with standard signal 4-20 mA;
   (all aforementioned elements from Rosemount/Emerson);

f) for $\dot{m}_P$:
   Prowirl 72 vortex flow meter from Endress+Hauser; D-79576 Weil am Rhein; data transfer to the PCS with standard signal 4-20 mA;
   the mass density of liquid phase P was recorded in the process computer at the value of 1060 g/dm³ as a constant;

g) for control of the substream to be fed to the coolant reservoir and to be withdrawn simultaneously:
   two control valves with nominal width DN100 of the Flow Top type from Flowserve, D-45141 Essen, data transfer from the PCS with standard signal 4-20 mA.

Beyond the division of the mass flow of the crystal suspension S withdrawn from the buffer tank between the two wash columns, but before entry of particular partial mass flow into the particular wash column was disposed in each case a Krohne MFM 7051K coriolis mass flow meter, which comprised an Optimass 7000 sensor element and a 051 K transducer. As an additional safety precaution, this was used to determine both the crystal suspension mass flow fed to the wash columns and its mass density (which in turn is a measure of the current degree of crystallization Y of the crystal suspension withdrawn from the buffer tank).

The data was transferred to the PCS with an (analog) standard signal 4-20 mA.

For $C_{Kr}$, $C_P^P$, $C_P^K$, $C_P^H$ and $\dot{Q}_D$ (were determined by means of a water run), the following constant values were recorded in all process computers:

$C_{Kr} = 178$ J/g;

$C_P^P = 1.97$ J/(g·K);

$C_P^K = 3.55$ J/(g·K);

$C_P^H = 3.55$ J/(g·K); and $\dot{Q}_D = 72$ MJ/h.

The starting conditions were a steady operating state of the two crystallizers, which was characterized by the following boundary conditions:

Target product X=acrylic acid.

Liquid phase P fed to the crystallizers=crude acrylic acid which originated from a fractional condensation of a product gas mixture of a two-stage heterogeneously catalyzed partial gas phase oxidation of chemical grade propylene to acrylic acid and had the following contents:
94.44% by weight of acrylic acid,
1.0105% by weight of acetic acid,
3.64% by weight of water,
0.0304% by weight of formic acid,
0.0346% by weight of formaldehyde,
0.0209% by weight of acrolein,
0.0945% by weight of propionic acid,
0.1061% by weight of furfurals,
0.0027% by weight of allyl acrylate,
0.0017% by weight of allyl formate,
0.0194% by weight of benzaldehyde,
0.1038% by weight of maleic anhydride,
0.4337% by weight of diacrylic acid,
0.0055% by weight of phenothiazine,
0.0192% by weight of MEHQ and
0.0003% by weight of molecular oxygen.

Operating State of Crystallizer 1:

| | |
|---|---|
| $T_K^{in} = 2.30°$ C.; | $T_K^{out} - T_K^{in} = 2.55$ K; |
| $T_K^{out} = 4.85°$ C.; | |
| $\dot{m}_K = 210.0$ t/h; | |
| $T_H^{in} = 12.03°$ C.; | $T_H^{out} - T_H^{in} = -1.67$ K; |
| $T_H^{out} = 10.36°$ C.; | |
| $\dot{m}_H = 42.5$ t/h; | |
| $T_P^{in} = 14.06°$ C.; | $T_S^{out} - T_P^{in} = -7.0$ K; |
| $T_S^{out} = 7.06°$ C.; | |
| $\dot{m}_P = 26.05$ t/h; | |

Operating State of Crystallizer 2:

| | |
|---|---|
| $T_K^{in} = 1.90°$ C.; | $T_K^{out} - T_K^{in} = 2.7$ K; |
| $T_K^{out} = 4.60°$ C.; | |
| $\dot{m}_K = 206.8$ t/h; | |
| $T_H^{in} = 12.03°$ C.; | $T_H^{out} - T_H^{in} = -1.67$ K; |
| $T_H^{out} = 10.36°$ C.; | |
| $\dot{m}_H = 44.0$ t/h; | |
| $T_P^{in} = 14.06°$ C.; | $T_S^{out} - T_P^{in} = -7.27$ K; |
| $T_S^{out} = 6.79°$ C.; | |
| $\dot{m}_P = 26.75$ t/h. | |

The mass density ρ of the crystal suspension S fed from the buffer vessel to the wash columns was from 1122.4 to 1122.7 g/cm³. This corresponded to a current degree of crystallization Y of 0.291.

The content in the mother liquor (liquid residual phase R) of acrylic acid in the suspension S was 92.34% by weight.

Proceeding from this steady operating state, $\dot{m}_P$ was, as shown in FIG. 1 for the two crystallizers with reference to curves 1 and 2, increased in order to satisfy an increased market demand.

The change in $\dot{m}_P$ was accompanied, as a result of production (inter alia, as a result of addition of acid water for the purpose of reducing the encrustation tendency (i.e. maintaining the cooling performance); acid water is an aqueous solution which is generally obtained in the course of conversion of acrylic acid from the product gas mixture of the partial oxidation to the condensed phase and comprises normally at least 60% by weight of water and at least 3% by weight of acrylic acid and secondary components (cf., for example, WO 2004/035514, DE-A 102 43 625, EP-A 1818324, DE-A 103 23 758 and German application No. 10 2007 004 960.0), by a change in the contents of the crude acrylic acid to the following values:

93.73% by weight of acrylic acid,
0.9792% by weight of acetic acid,
4.43% by weight of water,
0.0284% by weight of formic acid,
0.0305% by weight of formaldehyde,
0.0210% by weight of acrolein,
0.0904% by weight of propionic acid,
0.0965% by weight of furfural,
0.0025% by weight of allyl acrylate,
0.0015% by weight of allyl formate,
0.0178% by weight of benzaldehyde,
0.0972% by weight of maleic anhydride,
0.4048% by weight of diacrylic acid,
0.0071% by weight of phenothiazine,
0.0179% by weight of MEHQ, and
0.0003% by weight of molecular oxygen.

FIG. 1 likewise shows, in a representative manner, the profile of $T_K^{in}$ (curves 3 and 4) against time resulting from the change in $\dot{m}_P$, and also the course of the mass density of the suspension S (measured upstream of the wash columns, curves 5 and 6) over time until the new steady operating state is attained.

In FIG. 1, the abscissa is the time (8 scale parts correspond to 1½ h) and the ordinate shows $\dot{m}_P$ in t/h (curves 1 and 2), $T_K^{in}$ in ° C. (curves 3 and 4) and ρ in g/dm³ (curves 5 and 6). The point of intersection of the ordinate with the abscissa corresponds to 15 t/h for ($\dot{m}_P$);

−3° C. (for $T_K^{in}$); and 1090 g/dm³ (for ρ).

The end point of the ordinate corresponds to 35 t/h for ($\dot{m}_P$);

+7° C. (for $T_K^{in}$); and 1140 g/dm³ (for ρ).

Intermediate values on the ordinate can be interpolated in a linear manner between the two aforementioned points.

The ordinate values at half the ordinate length are therefore 25 t/h for ($\dot{m}_P$);

2° C. (for $T_K^{in}$); and 1115 g/dm³ (for ρ).

The substantial constancy of ρ over time reflects the excellent stability of Y in spite of a considerable abrupt change in $\dot{m}_P$. Overshooting of the closed-loop control of Y did not occur.

The purity of the glacial acrylic acid removed in the wash columns was >99.7% by weight over the entire operating time even though the increase in $\dot{m}_P$ had partly been passed on to the particular wash column.

The content in the mother liquor (in the liquid residual phase R) of acrylic acid in the suspension S was, after the increase in $\dot{m}_P$, 91.34% by weight.

U.S. Provisional Patent Application No. 60/971,969, filed Sep. 13, 2007, is incorporated in the present application by literature reference.

With regard to the abovementioned teachings, numerous changes and deviations from the present invention are possible. It can therefore be assumed that the invention, within the scope of the appended claims, can also be performed differently than the way specifically described herein.

The invention claimed is:

1. A process for continuously removing a target product X in the form of crystals of the target product X from a liquid phase P comprising the target product X and constituents other than the target product X with the aid of a heat exchanger having a secondary chamber and at least one primary chamber, in which the secondary chamber and the at least one primary chamber are each spatially separated from one another by at least one material dividing wall which serves as an area for transferring heat out of the secondary chamber into the at least one primary chamber, in which liquid phase P is conducted continuously into the secondary chamber of the heat exchanger, while the at least one primary chamber is simultaneously flowed through by at least one fluid cooling medium such that crystals of the target product X are formed from the liquid phase P in the secondary chamber to leave a liquid residual phase R and are suspended in the remaining liquid residual phase R which, compared to the liquid phase P, comprises the constituents other than the target product X in enriched form and whose content of target product X is at least 70% by weight to obtain a suspension S of crystals of the target product X in the liquid residual phase R which has a degree of crystallization Y, and suspension S is conducted continuously out of the secondary chamber of the heat exchanger, wherein variations in the desired degree of crystallization Y of the suspension S conducted out of the secondary chamber of the heat exchanger are minimized by determining and then minimizing the difference, determined at a particular operating time with the aid of a process computer, between (1) the flow of heat of crystallization $\dot{Q}_{Kr,Y}$ which develops in the secondary chamber according to the desired degree of crystallization Y, and (2) the difference formed between the heat flow $\dot{Q}_{out}$ otherwise conducted overall out of the secondary chamber of the heat exchanger and the heat flow $\dot{Q}_{in}$ otherwise conducted overall into the secondary chamber of the heat exchanger, and wherein the target product X is acrylic acid, methacrylic acid, p-xylene or N-vinylpyrrolidone.

2. The process according to claim 1, wherein the content in the liquid residual phase R of target product X is ≧80% by weight.

3. The process according to claim 1, wherein the content in the liquid residual phase R of target product X is ≧90% by weight.

4. The process according to claim 1, wherein the target product X is acrylic acid.

5. The process according to claim 1, wherein the liquid phase P comprises at least two constituents other than the target product X.

6. The process according to claim 1, wherein the liquid phase P is crude acrylic acid which has the following contents:
≧85% by weight of acrylic acid,
≧100 ppm by weight to ≦10% by weight of acetic acid,
≧10 ppm by weight to ≦5% by weight of propionic acid,
up to 5% by weight of low molecular weight aldehydes,
up to 3% by weight of polymerization inhibitors,
0 to 5% by weight of diacrylic acid, and
up to 10% by weight of water.

7. The process according to claim 1, which comprises, in addition to the process step according to claim 1, the following process steps:
b) separating the suspension S conducted out of the secondary chamber of the heat exchanger into crystals of the target product X and liquid residual phase R,
c) at least partly melting the crystals of the target product X removed and
d) at least partly recycling the molten crystals of the target product X to step b) and/or to the process step for continuous removal of target product X according to claim 1.

8. The process according to claim 1, which is followed by a process for continuously removing crystals of the target product X present in the suspension S, in which
the suspension S is fed to a wash column which has a wash column wall which surrounds a process chamber,
liquid residual phase R is released from the process chamber while retaining the crystals present in the suspension S to form a crystal bed in the process chamber from the suspension S conducted into the process chamber by means of filter equipment,
the crystal bed is conveyed within the process chamber,
at least one force other than gravity acts in the process chamber in the conveying direction of the crystal bed and conveys the crystal bed within the process chamber,
pure melt which consists of molten crystals which have been removed beforehand by this wash column process is conducted within the process chamber in countercurrent to the crystal bed such that a wash front which divides the crystal bed into a mother liquor zone and into a pure melt zone forms in the crystal bed, and
crystals in solid and/or molten form which have been washed in the wash column are discharged continuously at the opposite end of the wash column to the feed of the suspension S.

9. The process according to claim 8, wherein the target product is acrylic acid and the process is followed by a further process in which molten and removed acrylic acid crystals are subjected to a polymerization with themselves or with other at least monoethylenically unsaturated compounds.

10. The process according to claim 1, wherein the liquid phase P is conducted into the secondary chamber of the heat exchanger with the mass flow intensity $\dot{m}_P$ and the process comprises a determination of the mass flow intensity $\dot{m}_P$ and/or of the intensity of the volume flow corresponding to $\dot{m}_P$.

11. The process according to claim 10, wherein the mass flow intensity $\dot{m}_P$ is determined with the aid of a coriolis mass flow meter, or of a vortex flow meter, or of a magnetic-inductive flow meter, or of a variable area flow meter.

12. The process according to claim 1, wherein the liquid phase P is conducted into the secondary chamber with a temperature $T_P^{in}$ and the suspension S is conducted out of the secondary chamber with a temperature $T_S^{out}$, and the process comprises a determination of $T_P^{in}$, of $T_S^{out}$ and of $T_P^{in}-T_S^{out}$.

13. The process according to claim 12, wherein the determination of $T_P^{in}$ and of $T_S^{out}$ is carried out in each case with a resistance thermometer.

14. The process according to claim 13, wherein the resistance thermometer is a platinum resistance thermometer.

15. The process according to claim 1, wherein the fluid cooling medium flowing through the at least one primary chamber is conducted into the at least one primary chamber with a temperature $T_K^{in}$ and is conducted out of the at least one primary chamber with the temperature $T_K^{out}$, and the process comprises a determination of $T_K^{in}$, $T_K^{out}$ and of $T_K^{out}-T_K^{in}$.

16. The process according to claim 15, wherein the determination of $T_K^{in}$ and $T_K^{out}$ is carried out in each case with a resistance thermometer.

17. The process according to claim 16, wherein the resistance thermometer is a platinum resistance thermometer.

18. The process according to claim 15, wherein the determination of the difference of $T_K^{out}-T_K^{in}$ is carried out with two resistance thermometers and only one temperature difference transducer.

19. The process according to claim 18, wherein the temperature difference transducer is a fieldbus transducer.

20. The process according to claim 1, wherein the fluid cooling medium flowing through the at least one primary chamber is conducted into the at least one primary chamber with the mass flow intensity $\dot{m}_K$ and the process comprises a determination of the mass flow intensity $\dot{m}_K$ and/or the intensity of the volume flow accompanying $\dot{m}_K$.

21. The process according to claim 20, wherein the mass flow intensity $\dot{m}_K$ is determined with the aid of a coriolis mass flow meter, or of a vortex flow meter, or of a magnetic-inductive flow meter, or of a variable area flow meter.

22. The process according to claim 1, wherein the cooling medium which flows through the at least one primary chamber is conducted into the at least one primary chamber with the temperature $T_K^{in}$ and, in the case that the difference between $\dot{Q}_{Kr,Y}$ and the difference $\dot{Q}_{out}-\dot{Q}_{in}$ is not vanishing, $T_K^{in}$ is changed.

23. The process according to claim 1, wherein the target product X is acrylic acid which has been obtained by a heterogeneously catalyzed partial gas phase oxidation.

24. The process according to claim 1, wherein the target product X is acrylic acid, and the liquid phase P is derived from a fractional condensation and/or absorption of the product gas mixture of a heterogeneously catalyzed partial gas phase oxidation to prepare acrylic acid.

25. The process according to claim 1, wherein the heat exchanger is a cooling disk crystallizer.

26. The process according to claim 1, wherein the coolant used is a mixture of water and methanol or a mixture of water and glycol.

27. The process according to claim 1, which is followed by a determination of the mass density of the suspension S with the aid of a coriolis mass flow meter.

28. The process according to claim 1, wherein Y is from 0.10 to 0.50.

29. The process according to claim 1, wherein Y is from 0.20 to 0.40.

30. A process for preparing a target product X, which comprises carrying out the process according to claim 1, and recovering target product X.

31. A process for preparing a target product X, which comprises carrying out the process according to claim 10, and recovering target product X.

* * * * *